(12) United States Patent
Cox et al.

(10) Patent No.: US 7,176,007 B2
(45) Date of Patent: Feb. 13, 2007

(54) RECA MUTANTS

(75) Inventors: Michael M. Cox, Oregon, WI (US); Shelley L. Lusetti, Madison, WI (US); Aimee L. Eggler, Chicago, IL (US); Nami Haruta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 269 days.

(21) Appl. No.: 10/733,782

(22) Filed: Dec. 11, 2003

(65) Prior Publication Data

US 2004/0157248 A1 Aug. 12, 2004

Related U.S. Application Data

(60) Provisional application No. 60/432,758, filed on Dec. 12, 2002.

(51) Int. Cl.
*C12N 9/00* (2006.01)
*C07K 14/245* (2006.01)

(52) U.S. Cl. ........................ 435/183; 530/350
(58) Field of Classification Search ............ None
See application file for complete search history.

(56) References Cited

OTHER PUBLICATIONS

Larminat, F. et al., "Modulation of the SOS resposne by truncated RecA proteins", 1989, Mol. Gen. Genet., vol. 216: pp. 106-112.*
Ennis, D.G., et al., "Analysis of recA mutants with altered SOS functions," (1995) Mutat. Res. 336:39-48.
Knight, K.L., et al., "Identification of the Amino Acid Substitutions in Two Mutant Forms of the recA Protein from *Escherichia coli*: recA441 and recA629*," (1984) J. Biol. Chem. 259:11279-11283.
Lavery, P.E., et al., "Biochemical Basis of the Constitutive Repressor Cleavage Activity of recA730 Protein," (1992) J. of Biol. Chem. 267:20648-20658.
Lusetti, S.L., et al., "C-terminal Deletions of the *Escherichia coli* RecA Protein," (2003) J. Biol. Chem. 278:16372-16380.
Lusetti, S.L., et al., "Magnesium Ion-dependent Acticator of the RecA Protein Involves the C Terminus," (2003) J. Biol. Chem. 278:16381-16388.
Madiraju, M.V., et al., "Properties of a Mutant recA-Encoded Protein Reveal a Possible Role for *Escherichia coli* recF-Encoded Protein in Genetic Recombination," (1988) Proc. Natl. Acad. Sci. U.S.A. 85:6592-6596.
Madiraju, M.V., et al., "Enzymatic Properties of the RecA803 Protein, a Partial Suppressor of recF Mutations," (1992) Biochemistry 31:10529-10535.
Shan, Q., et al., "DNA Strand Exchange Promoted by RecA K72R," (1996) J. Biol. Chem. 271:5712-5724.
Tateishi, S., et al., "C-terminal Truncated *Escherichia coli* RecA Protein RecA5327 Has Enhanced Binding Affinities to Single- and Double-stranded DNAs," (1992) J. Mol. Biol. 223:115-129.
Thomas, A., et al., "Control of recA dependent activities in *Escherichia coli*: a possible role for the recF product," (1983) J. Gen. Microbiol. 129:681-686.
Volkert, M.R., et al., "Two-Componenet Suppression of recF143 by recA441 in *Escherichia coli* K-12," (1984) J. Bact. 160:702-705.
Wang, T.C., et al., "recA (Srf) Suppression of recF Deficiency in the Postreplication Repair of UV-Irradiated *Escherichia coli* K-12," (1986) J. Bact. 168:940-946.
Wang, T.C., et al., "Cloning and preliminary characterization of srf-2020 and srf-801, the recF partial suppressor mutations which map in recA of *Escherichia coli* K-12," (1991) Biochimie 73:335-340.
Wang, T.C., et al., "Cosuppression of recF, recR and recO mutations by mutant recA alleles in *Escherichia coli* cells," (1993) Mutat. Res. 294:157-166.

* cited by examiner

*Primary Examiner*—Scott D. Priebe
*Assistant Examiner*—Michael Burkhart
(74) *Attorney, Agent, or Firm*—Quarles & Brady LLP

(57) ABSTRACT

The present invention provides RecA mutant proteins, having either a single mutation or a double mutation. The RecA mutant proteins are highly proficient in both SSB displacement and steady state binding of DNA in the presence or absence of SSB as compared to the wild-type protein. The single RecA mutant, RecAΔC17, has 17 amino acid residues removed from the carboxyl terminus. The double mutant RecA, RecAΔC17/E38K, combines the 17 amino acid residue C-terminal deletion of RecAΔC17, with a single amino acid change from Glutamate to Lysine at position 38. These RecA mutant proteins are pH sensitive allowing control over formation of products. Hence, methods of using the novel RecA mutants and kits having the RecA mutants as components thereof are also contemplated by the present invention.

24 Claims, 15 Drawing Sheets

AIDENKQKA LAAALGQIEK QFGKGSIMRL GEDRSMDVET ISTGSLSLDI

ALGAGGLPMG RIVEIYGPES SGKTTLTLQV IAAAQREGKT CAFIDAEHAL

DPIYARKLGV DIDNLLCSQP DTGEQALEIC DALARSGAVD VIVVDSVAAL

TPKAEIEGEI GDSHMGLAAR MMSQAMRKLA GNLKQSNTLL IFINQIRMKI

GVMFGNPETT TGGNALKFYA SVRLDIRRIG AVKEGENVVG SETRVKVVKN

KIAAPFKQAE FQILYGEGIN FYGELVDLGV KEKLIEKAGA WYSYKGEKIG

QGKANATAWL KDNPETAKEI EKKVRELLLS NPNSTP         SEQ ID NO:1

FIG 11

```
   1 ATGGCTATCG ACGAAAACAA ACAGAAAGCG TTGGCGGCAG CACTGGGCCA
  51 GATTGAGAAA CAATTTGGTA AAGGCTCCAT CATGCGCCTG GGTGAAGACC
 101 GTTCAATGGA TGTGGAAACC ATCTCTACCG GTTCGCTTTC ACTGGATATC
 151 GCGCTTGGGG CAGGTGGTCT GCCGATGGGC CGTATCGTCG AGATCTACGG
 201 ACCGGAATCT TCCGGTAAAA CCACGCTGAC GCTGCAGGTG ATCGCCGCAG
 251 CGCAGCGTGA AGGTAAAACC TGTGCGTTTA TCGATGCTGA ACACGCGCTG
 301 GACCCAATCT ACGCACGTAA ACTGGGCGTC GATATCGACA ACCTGCTGTG
 351 CTCCCAGCCG GACACCGGCG AGCAGGCACT GGAAATCTGT GACGCCCTGG
 401 CGCGTTCTGG CGCAGTAGAC GTTATCGTCG TTGACTCCGT GGCGGCACTG
 451 ACGCCGAAAG CGGAAATCGA AGGCGAAATC GGCGACTCTC ACATGGGCCT
 501 TGCGGCACGT ATGATGAGCC AGGCGATGCG TAAGCTGGCG GGTAACCTGA
 551 AGCAGTCCAA CACGCTGCTG ATCTTCATCA ACCAGATCCG TATGAAAATT
 601 GGTGTGATGT TCGGTAACCC GGAAACCACT ACCGGTGGTA ACGCGCTGAA
 651 ATTCTACGCC TCTGTTCGTC TCGACATCCG TCGTATCGGC GCGGTGAAAG
 701 AGGGCGAAAA CGTGGTGGGT AGCGAAACCC GCGTGAAAGT GGTGAAGAAC
 751 AAAATCGCTG CGCCGTTTAA ACAGGCTGAA TTCCAGATCC TCTACGGCGA
 801 AGGTATCAAC TTCTACGGCG AACTGGTTGA CCTGGGCGTA AAAGAGAAGC
 851 TGATCGAGAA AGCAGGCGCG TGGTACAGCT ACAAAGGTGA AAGATCGGT
 901 CAGGGTAAAG CGAATGCGAC TGCCTGGCTG AAAGATAACC CGGAAACCGC
 951 GAAAGAGATC GAGAAGAAAG TACGTGAGTT GCTGCTGAGC AACCCGAACT
1001 CAACGCCGTA A    SEQ ID NO:2
```

FIG 12

```
AIDENKQKA  LAAALGQIEK  QFGKGSIMRL  GEDRSMDVKT  ISTGSLSLDI

ALGAGGLPMG  RIVEIYGPES  SGKTTLTLQV  IAAAQREGKT  CAFIDAEHAL

DPIYARKLGV  DIDNLLCSQP  DTGEQALEIC  DALARSGAVD  VIVVDSVAAL

TPKAEIEGEI  GDSHMGLAAR  MMSQAMRKLA  GNLKQSNTLL  IFINQIRMKI

GVMFGNPETT  TGGNALKFYA  SVRLDIRRIG  AVKEGENVVG  SETRVKVVKN

KIAAPFKQAE  FQILYGEGIN  FYGELVDLGV  KEKLIEKAGA  WYSYKGEKIG

QGKANATAWL  KDNPETAKEI  EKKVRELLLS  NPNSTP*     SEQ ID NO:3
```

FIG 13

```
   1 ATGGCTATCG ACGAAAACAA ACAGAAAGCG TTGGCGGCAG CACTGGGCCA
  51 GATTGAGAAA CAATTTGGTA AAGGCTCCAT CATGCGCCTG GGTGAAGACC
 101 GTTCCATGGA TGTGAAAACC ATCTCTACCG GTTCGCTTTC ACTGGATATC
 151 GCGCTTGGGG CAGGTGGTCT GCCGATGGGC CGTATCGTCG AGATCTACGG
 201 ACCGGAATCT TCCGGTAAAA CCACGCTGAC GCTGCAGGTG ATCGCCGCAG
 251 CGCAGCGTGA AGGTAAAACC TGTGCGTTTA TCGATGCTGA ACACGCGCTG
 301 GACCCAATCT ACGCACGTAA ACTGGGCGTC GATATCGACA ACCTGCTGTG
 351 CTCCCAGCCG GACACCGGCG AGCAGGCACT GGAAATCTGT GACGCCCTGG
 401 CGCGTTCTGG CGCAGTAGAC GTTATCGTCG TTGACTCCGT GGCGGCACTG
 451 ACGCCGAAAG CGGAAATCGA AGGCGAAATC GGCGACTCTC ACATGGGCCT
 501 TGCGGCACGT ATGATGAGCC AGGCGATGCG TAAGCTGGCG GGTAACCTGA
 551 AGCAGTCCAA CACGCTGCTG ATCTTCATCA ACCAGATCCG TATGAAAATT
 601 GGTGTGATGT TCGGTAACCC GGAAACCACT ACCGGTGGTA ACGCGCTGAA
 651 ATTCTACGCC TCTGTTCGTC TCGACATCCG TCGTATCGGC GCGGTGAAAG
 701 AGGGCGAAAA CGTGGTGGGT AGCGAAACCC GCGTGAAAGT GGTGAAGAAC
 751 AAAATCGCTG CGCCGTTTAA ACAGGCTGAA TTCCAGATCC TCTACGGCGA
 801 AGGTATCAAC TTCTACGGCG AACTGGTTGA CCTGGGCGTA AAAGAGAAGC
 851 TGATCGAGAA AGCAGGCGCG TGGTACAGCT ACAAGGTGAA GAAGATCGGT
 901 CAGGGTAAAG CGAATGCGAC TGCCTGGCTG AAAGATAACC CGGAAACCGC
 951 GAAAGAGATC GAGAAGAAAG TACGTGAGTT GCTGCTGAGC AACCCGAACT
1001 CAACGCCGTA A     SEQ ID NO:4
```

FIG 14

AIDENKQKA LAAALGQIEK QFGKGSIMRL GEDRSMDVET ISTGSLSLDI

ALGAGGLPMG RIVEIYGPES SGKTTLTLQV IAAAQREGKT CAFIDAEHAL

DPIYARKLGV DIDNLLCSQP DTGEQALEIC DALARSGAVD VIVVDSVAAL

TPKAEIEGEI GDSHMGLAAR MMSQAMRKLA GNLKQSNTLL IFINQIRMKI

GVMFGNPETT TGGNALKFYA SVRLDIRRIG AVKEGENVVG SETRVKVVKN

KIAAPFKQAE FQILYGEGIN FYGELVDLGV KEKLIEKAGA WYSYKGEKIG

QGKANATAWL KDNPETAKEI EKKVRELLLS NPNSTPDFSV DDSEGVAETN EDF

SEQ ID NO: 5

FIG 15

```
                        SEQUENCE LISTING

<160> NUMBER OF SEQ ID NOS: 5

<210> SEQ ID NO 1
<211> LENGTH: 335
<212> TYPE: PRT
<213> ORGANISM: Escherichia coli

<400> SEQUENCE: 1

Ala Ile Asp Glu Asn Lys Gln Lys Ala Leu Ala Ala Ala Leu Gly Gln
1               5                   10                  15

Ile Glu Lys Gln Phe Gly Lys Gly Ser Ile Met Arg Leu Gly Glu Asp
            20                  25                  30

Arg Ser Met Asp Val Glu Thr Ile Ser Thr Gly Ser Leu Ser Leu Asp
        35                  40                  45

Ile Ala Leu Gly Ala Gly Gly Leu Pro Met Gly Arg Ile Val Glu Ile
    50                  55                  60

Tyr Gly Pro Glu Ser Ser Gly Lys Thr Thr Leu Thr Leu Gln Val Ile
65                  70                  75                  80

Ala Ala Ala Gln Arg Glu Gly Lys Thr Cys Ala Phe Ile Asp Ala Glu
                85                  90                  95

His Ala Leu Asp Pro Ile Tyr Ala Arg Lys Leu Gly Val Asp Ile Asp
            100                 105                 110

Asn Leu Leu Cys Ser Gln Pro Asp Thr Gly Glu Gln Ala Leu Glu Ile
        115                 120                 125

Cys Asp Ala Leu Ala Arg Ser Gly Ala Val Asp Val Ile Val Val Asp
    130                 135                 140

Ser Val Ala Ala Leu Thr Pro Lys Ala Glu Ile Glu Gly Glu Ile Gly
145                 150                 155                 160

Asp Ser His Met Gly Leu Ala Ala Arg Met Met Ser Gln Ala Met Arg
```

```
                       165                 170                 175
Lys Leu Ala Gly Asn Leu Lys Gln Ser Asn Thr Leu Leu Ile Phe Ile
                180                 185                 190
Asn Gln Ile Arg Met Lys Ile Gly Val Met Phe Gly Asn Pro Glu Thr
            195                 200                 205
Thr Thr Gly Gly Asn Ala Leu Lys Phe Tyr Ala Ser Val Arg Leu Asp
        210                 215                 220
Ile Arg Arg Ile Gly Ala Val Lys Glu Gly Glu Asn Val Val Gly Ser
225                 230                 235                 240
Glu Thr Arg Val Lys Val Val Lys Asn Lys Ile Ala Ala Pro Phe Lys
                245                 250                 255
Gln Ala Glu Phe Gln Ile Leu Tyr Gly Glu Gly Ile Asn Phe Tyr Gly
            260                 265                 270
Glu Leu Val Asp Leu Gly Val Lys Glu Lys Leu Ile Glu Lys Ala Gly
        275                 280                 285
Ala Trp Tyr Ser Tyr Lys Gly Glu Lys Ile Gly Gln Gly Lys Ala Asn
            290                 295                 300
Ala Thr Ala Trp Leu Lys Asp Asn Pro Glu Thr Ala Lys Glu Ile Glu
305                 310                 315                 320
Lys Lys Val Arg Glu Leu Leu Leu Ser Asn Pro Asn Ser Thr Pro
                325                 330                 335
```

<210> SEQ ID NO 2
<211> LENGTH: 1011
<212> TYPE: DNA
<213> ORGANISM: Escherichia coli

<400> SEQUENCE: 2

```
atggctatcg acgaaaacaa acagaaagcg ttggcggcag cactgggcca gattgagaaa      60
caatttggta aaggctccat catgcgcctg ggtgaagacc gttcaatgga tgtggaaacc     120
atctctaccg gttcgctttc actggatatc gcgcttgggg caggtggtct gccgatgggc     180
cgtatcgtcg agatctacgg accggaatct tccggtaaaa ccacgctgac gctgcaggtg     240
atcgccgcag cgcagcgtga aggtaaaacc tgtgcgtttt cgatgctga acacgcgctg     300
gacccaatct acgcacgtaa actgggcgtc gatatcgaca acctgctgtg ctcccagccg     360
gacaccggcg agcaggcact ggaaatctgt gacgccctgg cgcgttctgg cgcagtagac     420
gttatcgtcg ttgactccgt ggcggcactg acgccgaaag cggaaatcga aggcgaaatc     480
ggcgactctc acatgggcct tgcggcacgt atgatgagcc aggcgatgcg taagctggcg     540
ggtaacctga gcagtccaa cacgctgctg atcttcatca accagatccg tatgaaaatt     600
ggtgtgatgt tcggtaaccc ggaaaccact accggtggta acgcgctgaa attctacgcc     660
tctgttcgtc tcgacatccg tcgtatcggc gcggtgaaag agggcgaaaa cgtggtgggt     720
agcgaaaccc gcgtgaaagt ggtgaagaac aaaatcgctg cgccgtttaa acaggctgaa     780
ttccagatcc tctacggcga aggtatcaac ttctacggcg aactggttga cctgggcgta     840
aaagagaagc tgatcgagaa agcaggcgcg tggtacagct acaaaggtga aaagatcggt     900
cagggtaaag cgaatgcgac tgcctggctg aaagataacc cggaaaccgc gaaagagatc     960
gagaagaaag tacgtgagtt gctgctgagc aacccgaact caacgccgta a             1011
```

<210> SEQ ID NO 3
<211> LENGTH: 335

```
<212> TYPE: PRT
<213> ORGANISM: Escherichia coli

<400> SEQUENCE: 3

Ala Ile Asp Glu Asn Lys Gln Lys Ala Leu Ala Ala Leu Gly Gln
1               5                   10                  15

Ile Glu Lys Gln Phe Gly Lys Gly Ser Ile Met Arg Leu Gly Glu Asp
            20                  25                  30

Arg Ser Met Asp Val Lys Thr Ile Ser Thr Gly Ser Leu Ser Leu Asp
            35                  40                  45

Ile Ala Leu Gly Ala Gly Gly Leu Pro Met Gly Arg Ile Val Glu Ile
50                  55                  60

Tyr Gly Pro Glu Ser Ser Gly Lys Thr Thr Leu Thr Leu Gln Val Ile
65                  70                  75                  80

Ala Ala Ala Gln Arg Glu Gly Lys Thr Cys Ala Phe Ile Asp Ala Glu
                85                  90                  95

His Ala Leu Asp Pro Ile Tyr Ala Arg Lys Leu Gly Val Asp Ile Asp
            100                 105                 110

Asn Leu Leu Cys Ser Gln Pro Asp Thr Gly Glu Gln Ala Leu Glu Ile
        115                 120                 125

Cys Asp Ala Leu Ala Arg Ser Gly Ala Val Asp Val Ile Val Val Asp
130                 135                 140

Ser Val Ala Ala Leu Thr Pro Lys Ala Glu Ile Glu Gly Glu Ile Gly
145                 150                 155                 160

Asp Ser His Met Gly Leu Ala Ala Arg Met Met Ser Gln Ala Met Arg
                165                 170                 175

Lys Leu Ala Gly Asn Leu Lys Gln Ser Asn Thr Leu Leu Ile Phe Ile
            180                 185                 190

Asn Gln Ile Arg Met Lys Ile Gly Val Met Phe Gly Asn Pro Glu Thr
        195                 200                 205

Thr Thr Gly Gly Asn Ala Leu Lys Phe Tyr Ala Ser Val Arg Leu Asp
210                 215                 220

Ile Arg Arg Ile Gly Ala Val Lys Glu Gly Glu Asn Val Val Gly Ser
225                 230                 235                 240

Glu Thr Arg Val Lys Val Val Lys Asn Lys Ile Ala Ala Pro Phe Lys
                245                 250                 255

Gln Ala Glu Phe Gln Ile Leu Tyr Gly Glu Gly Ile Asn Phe Tyr Gly
            260                 265                 270

Glu Leu Val Asp Leu Gly Val Lys Glu Lys Leu Ile Glu Lys Ala Gly
        275                 280                 285

Ala Trp Tyr Ser Tyr Lys Gly Glu Lys Ile Gly Gln Gly Lys Ala Asn
290                 295                 300

Ala Thr Ala Trp Leu Lys Asp Asn Pro Glu Thr Ala Lys Glu Ile Glu
305                 310                 315                 320

Lys Lys Val Arg Glu Leu Leu Leu Ser Asn Pro Asn Ser Thr Pro
                325                 330                 335

<210> SEQ ID NO 4
<211> LENGTH: 1011
<212> TYPE: DNA
<213> ORGANISM: Escherichia coli

<400> SEQUENCE: 4
atggctatcg acgaaaacaa acagaaagcg ttggcggcag cactgggcca gattgagaaa    60
caatttggta aaggctccat catgcgcctg ggtgaagacc gttccatgga tgtgaaaacc   120
```

-continued

```
atctctaccg gttcgctttc actggatatc gcgcttgggg caggtggtct gccgatgggc      180
cgtatcgtcg agatctacgg accggaatct tccggtaaaa ccacgctgac gctgcaggtg      240
atcgccgcag cgcagcgtga aggtaaaacc tgtgcgttta tcgatgctga acacgcgctg      300
gacccaatct acgcacgtaa actgggcgtc gatatcgaca acctgctgtg ctcccagccg      360
gacaccggcg agcaggcact ggaaatctgt gacgccctgg cgcgttctgg cgcagtagac      420
gttatcgtcg ttgactccgt ggcggcactg acgccgaaag cggaaatcga aggcgaaatc      480
ggcgactctc acatgggcct tgcggcacgt atgatgagcc aggcgatgcg taagctggcg      540
ggtaacctga agcagtccaa cacgctgctg atcttcatca accagatccg tatgaaaatt      600
ggtgtgatgt tcggtaaccc ggaaaccact accggtggta acgcgctgaa attctacgcc      660
tctgttcgtc tcgacatccg tcgtatcggc gcggtgaaag agggcgaaaa cgtggtgggt      720
agcgaaaccc gcgtgaaagt ggtgaagaac aaaatcgctg cgccgtttaa acaggctgaa      780
ttccagatcc tctacggcga aggtatcaac ttctacggcg aactggttga cctgggcgta      840
aaagagaagc tgatcgagaa agcaggcgcg tggtacagct acaaaggtga agatcggt       900 cagggtaaag cgaatgcgac tgcctggctg aaagataacc cggaaaccgc gaaagagatc      960
gagaagaaag tacgtgagtt gctgctgagc aacccgaact caacgccgta a              1011
```

<210> SEQ ID NO 5
<211> LENGTH: 352
<212> TYPE: PRT
<213> ORGANISM: Escherichia coli

<400> SEQUENCE: 5

```
Ala Ile Asp Glu Asn Lys Gln Lys Ala Leu Ala Ala Leu Gly Gln
1               5                   10                  15

Ile Glu Lys Gln Phe Gly Lys Gly Ser Ile Met Arg Leu Gly Glu Asp
            20                  25                  30

Arg Ser Met Asp Val Glu Thr Ile Ser Thr Gly Ser Leu Ser Leu Asp
        35                  40                  45

Ile Ala Leu Gly Ala Gly Gly Leu Pro Met Gly Arg Ile Val Glu Ile
    50                  55                  60

Tyr Gly Pro Glu Ser Ser Gly Lys Thr Thr Leu Thr Leu Gln Val Ile
65                  70                  75                  80

Ala Ala Ala Gln Arg Glu Gly Lys Thr Cys Ala Phe Ile Asp Ala Glu
                85                  90                  95

His Ala Leu Asp Pro Ile Tyr Ala Arg Lys Leu Gly Val Asp Ile Asp
            100                 105                 110

Asn Leu Leu Cys Ser Gln Pro Asp Thr Gly Glu Gln Ala Leu Glu Ile
        115                 120                 125

Cys Asp Ala Leu Ala Arg Ser Gly Ala Val Asp Val Ile Val Val Asp
    130                 135                 140

Ser Val Ala Ala Leu Thr Pro Lys Ala Glu Ile Glu Gly Glu Ile Gly
145                 150                 155                 160

Asp Ser His Met Gly Leu Ala Ala Arg Met Met Ser Gln Ala Met Arg
                165                 170                 175

Lys Leu Ala Gly Asn Leu Lys Gln Ser Asn Thr Leu Leu Ile Phe Ile
            180                 185                 190

Asn Gln Ile Arg Met Lys Ile Gly Val Met Phe Gly Asn Pro Glu Thr
        195                 200                 205

Thr Thr Gly Gly Asn Ala Leu Lys Phe Tyr Ala Ser Val Arg Leu Asp
```

-continued

```
              210                 215                 220
Ile Arg Arg Ile Gly Ala Val Lys Glu Gly Glu Asn Val Val Gly Ser
225                 230                 235                 240

Glu Thr Arg Val Lys Val Val Lys Asn Lys Ile Ala Ala Pro Phe Lys
                245                 250                 255

Gln Ala Glu Phe Gln Ile Leu Tyr Gly Glu Gly Ile Asn Phe Tyr Gly
                260                 265                 270

Glu Leu Val Asp Leu Gly Val Lys Glu Lys Leu Ile Glu Lys Ala Gly
                275                 280                 285

Ala Trp Tyr Ser Tyr Lys Gly Glu Lys Ile Gly Gln Gly Lys Ala Asn
                290                 295                 300

Ala Thr Ala Trp Leu Lys Asp Asn Pro Glu Thr Ala Lys Glu Ile Glu
305                 310                 315                 320

Lys Lys Val Arg Glu Leu Leu Leu Ser Asn Pro Asn Ser Thr Pro Asp
                325                 330                 335

Phe Ser Val Asp Asp Ser Glu Gly Val Ala Glu Thr Asn Glu Asp Phe
                340                 345                 350
```

RECA MUTANTS

CROSS-REFERENCE TO RELATED APPLICATIONS

This application claims the priority benefit of U.S. Provisional Application Ser. No. 60/432,758, filed Dec. 12, 2002, incorporated by reference herein.

STATEMENT REGARDING FEDERALLY SPONSORED RESEARCH OR DEVELOPMENT

This invention was made with United States government support awarded by the following agency: NIH Grant Nos. GM 32335 and GM52725. The United States has certain rights in this invention.

BACKGROUND OF THE INVENTION

RecA protein catalyzes homologous DNA pairing and strand exchange reactions that are the central processes of recombination and recombinational DNA repair in all cells. The structure of the RecA protein of Escherichia coli (Mr 37,842) features three distinct domains (32–34, the contents of which is incorporated by reference here in its entirety). The core domain (residues 31–269) includes the ATP and DNA binding sites. The core is flanked by smaller N- and C-terminal domains. The C-terminal domains (residues 270–352) appear as distinct lobes on the surface of RecA filaments, which shift position markedly in response to the presence of different bound nucleotides (35,36). The far C-terminus of the RecA protein (defined here as the C-terminal 25 amino acid residues) exhibits a preponderance of negatively charged amino acids, with seven Glu or Asp residues in the terminal 17 residues. This function of this region has been explored with the use of C-terminal deletions (37–42). Several of these studies documented the in vitro effects of deleting all or most of the C-terminal 25 amino acid residues. The major effects were an improvement of binding to dsDNA (37–39) and an evident alteration of the conformation of the core domain (42).

Currently a main function of RecA is strand exchange which is initiated when RecA binds to single-stranded DNA (ssDNA) within a gap or a ssDNA terminal extension. RecA protein binds DNA in at least two steps. The first is a slow nucleation step (1–3), and this is followed by a rapid, cooperative binding of additional monomers to lengthen the filament uniquely in a 5' to 3' direction (4,5). The resulting RecA-ssDNA complex has an extended, helical conformation, with approximately 6 RecA monomers and 18 nucleotides (nt) of DNA per right-handed helical turn (18.6 base pairs per turn in RecA filaments with bound ATPγS (6)). This nucleoprotein filament can pair the bound single strand with the complementary strand of an incoming duplex, resulting in homologous recombination.

The ssDNA binding protein from E. coli, SSB, affects formation of the nucleoprotein filament in several ways. In vitro, under standard reaction conditions that generally include 8–12 mM $Mg^{2+}$, SSB stimulates filament formation on ssDNA substrates derived from bacteriophages by binding to and denaturing regions of secondary structure in the ssDNA that would otherwise hinder RecA filament extension (7). SSB is then displaced by the growing RecA filament (8). SSB thus permits the formation of a contiguous extended filament on the DNA. However, RecA and SSB bind ssDNA competitively in vitro, such that when SSB is prebound to ssDNA, it inhibits the nucleation stage of RecA protein filament formation (9,10). Subsequent binding of RecA to ssDNA results either when SSB transiently vacates a region of ssDNA, or when the RecOR mediator proteins facilitate RecA nucleation onto SSB-coated ssDNA (5,11, 12).

Genetic studies also indicate that SSB inhibits RecA filament formation and subsequent homologous recombination. SSB protein has multiple DNA binding modes, and interconversion between them is mediated by salt concentrations (29–31). Mutations in recF, recO or recR genes, which belong to the same epistasis group, result in defects in the repair of stalled replication forks (13–18). These defects are likely due at least in part to the inability of RecA protein to displace SSB from the single-stranded region of the stalled fork. In support of this model, overproduction of SSB leads to a sensitivity to UV-inflicted DNA damage that is similar to the phenotype of recF mutants (19). Additional evidence supports a competition between RecA and SSB for ssDNA in vivo. The recF, recO or recR phenotypes can be partially suppressed, and the suppressor mutations map to the recA gene. These recA mutants include recA803 (V37M) (20, the contents of which is incorporated by reference here in its entirety), recA2020 (T121I) (21 and 22, the contents of both is incorporated by reference), recA441 (E38K+ I298V) (23–25, the contents of each is incorporated by reference), and recA730 (E38K) (26 and 27, the contents of both is incorporated by reference). These RecA mutant proteins would need to be able to compensate in some way for the loss of the RecFOR proteins, and indeed RecA803, RecA441, and RecA E38K proteins all exhibit an enhanced ability to compete with SSB in vitro (8 and 28, the contents of both is incorporated by reference). RecA E38K protein competes best with SSB, followed by RecA441 and then RecA803 (8, the contents of which is incorporated by reference here in its entirety). However, these RecA mutants do not effectively displace SSB from linear single stranded DNA.

Indeed, Benedict and Kowalczykowski describe a study of a proteolytic fragment of RecA protein missing about 15% of the protein, which turned up in one purification prep of RecA protein. Although, some improved binding to duplex DNA was noted, the exact nature of the C-terminal deletion, greater than 25 amino acids, was never determined. Furthermore, no group has been able to reproduce the results since they did not report how many amino acids were deleted (37).

Likewise, Tateishi, et al. (38, the contents of which is incorporated by reference), describe a study of a purified RecA protein without 25 amino acids from the C-terminus. The authors also note some improved DNA binding. However, it has been found in work elaborated below that the described protein is still much less stable than RecA deletions desired for a variety of biological applications.

Also, Lavery and Kowalczykowski describe a study of the E38K mutant alone (called RecA730). The authors note some improved displacement of SSB using the RecA730. However, for many applications, their results still indicate a substantial lag in the binding to DNA and displacement of SSB by RecA730.

Larminat and Defais, also studied a carboxyl terminal deletion of 17 amino acids in vivo. However, the mutant was never actually isolated and characterized as a pure protein (41). Furthermore, Yu and Egelman, disclose use of a pure RecA mutant with an 18 amino acid deletion. However, the study was confined to the structure of the resulting filaments. Thus, in neither of these two papers was the biochemistry of these proteins actually explored (42).

Thus, a RecA mutant protein is desired which can catalyze homologous DNA pairing and strand exchange reactions more efficiently due to an enhanced capacity of the mutant protein to compete with SSB and to provide a more persistent binding of the mutant protein to DNA.

BRIEF SUMMARY OF THE INVENTION

The invention is based upon the discovery that when certain mutations are made to the RecA protein, the resultant mutant proteins are rendered highly proficient in SSB displacement and steady state binding of DNA as compared to the wild-type RecA protein in the presence or absence of a DNA binding protein.

Accordingly, the present invention features a variety of RecA mutant proteins with highly desirable enzymatic properties suitable for use in a variety of methods and related kits for practicing the invention.

In one aspect the invention provides a single mutant RecA protein having a deletion of at least 13–20 amino acid residues from the carboxyl terminus.

In another aspect the invention provides a single mutant RecA protein with 17 amino acids residues deleted from the carboxyl terminus.

In another aspect the invention provides a single mutant RecA protein having an enhanced capacity to displace a DNA binding protein, such as for example, SSB or RPA as compared to wild-type RecA.

In another aspect the invention provides a single mutant RecA protein exhibiting enhanced binding to DNA during a DNA strand exchange reaction as compared to wild-type RecA, wherein the DNA is single-stranded or may contain a secondary structure.

In another aspect the invention provides a double mutant RecA protein having a deletion of at least 13–25 amino acid residues from the carboxyl terminus and the amino acid change from a glutamate to a basic amino acid at position 38.

In another aspect the invention provides a double mutant RecA protein having a 17 amino acid residue deletion from the carboxyl terminus and the amino acid change from a glutamate to either lysine or arginine at position 38.

In another aspect the invention provides a polynucleotide sequence encoding the protein of either the single or double mutants of the invention.

In another aspect the invention provides a double mutant RecA protein having an enhanced capacity to displace a DNA binding protein, such as for example, SSB or RPA as compared to wild-type RecA.

In another aspect the invention provides a double mutant RecA protein having an increased steady-state DNA binding capacity during a DNA strand exchange reaction as compared to wild-type RecA, wherein the DNA is single-stranded, double-stranded, linear or circular; and wherein the reaction is pH and $Mg^{2+}$ concentration dependent.

In another aspect the invention provides a double mutant RecA protein which allows the RecA reaction to be regulated in a pH-dependent fashion, with late stages of DNA strand exchange being precluded at pHs below 7.0.

In another aspect the invention provides a double mutant RecA protein, which can promote a multiple-strand DNA exchange reaction.

In another aspect the invention provides a method of catalyzing homologous DNA pairing and DNA strand exchange reactions in an in vitro or in vivo environment using a sufficient amount of either the single or double mutant RecA protein of the invention.

Yet in another aspect the invention provides a kit including either the single or double mutant of the invention.

It is believed that the tight DNA-binding RecA mutants of the invention have the potential to enhance all current biotechnology applications using RecA protein and for making new applications feasible. Among the new applications will be the use of the tight-binding single and double mutants of the invention to promote in vitro alterations of genes to permit the rapid construction of desired gene mutants for industrial and pharmaceutical purposes. Other applications where the RecA mutants of the invention may be useful are described in detail below.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages and features of the present invention will become apparent from the following specification taken in conjunction with the accompanying drawings.

BRIEF DESCRIPTION OF THE SEVERAL VIEWS OF THE DRAWINGS

FIG. 11 shows the amino acid sequence for RecAΔC17 (SEQ ID NO:1).

FIG. 12 shows the polynucleotide sequence for RecAΔC17 (SEQ ID NO:2).

FIG. 13 shows the amino acid sequence for RecAE38K/ ΔC17 (SEQ ID NO:3).

FIG. 14 shows the polynucleotide sequence for RecAE38K/ΔC17 (SEQ ID NO:4).

FIG. 15 shows the amino acid sequence for the wild-type RecA (SEQ ID NO:5).

DETAILED DESCRIPTION OF THE INVENTION

Figure 1:
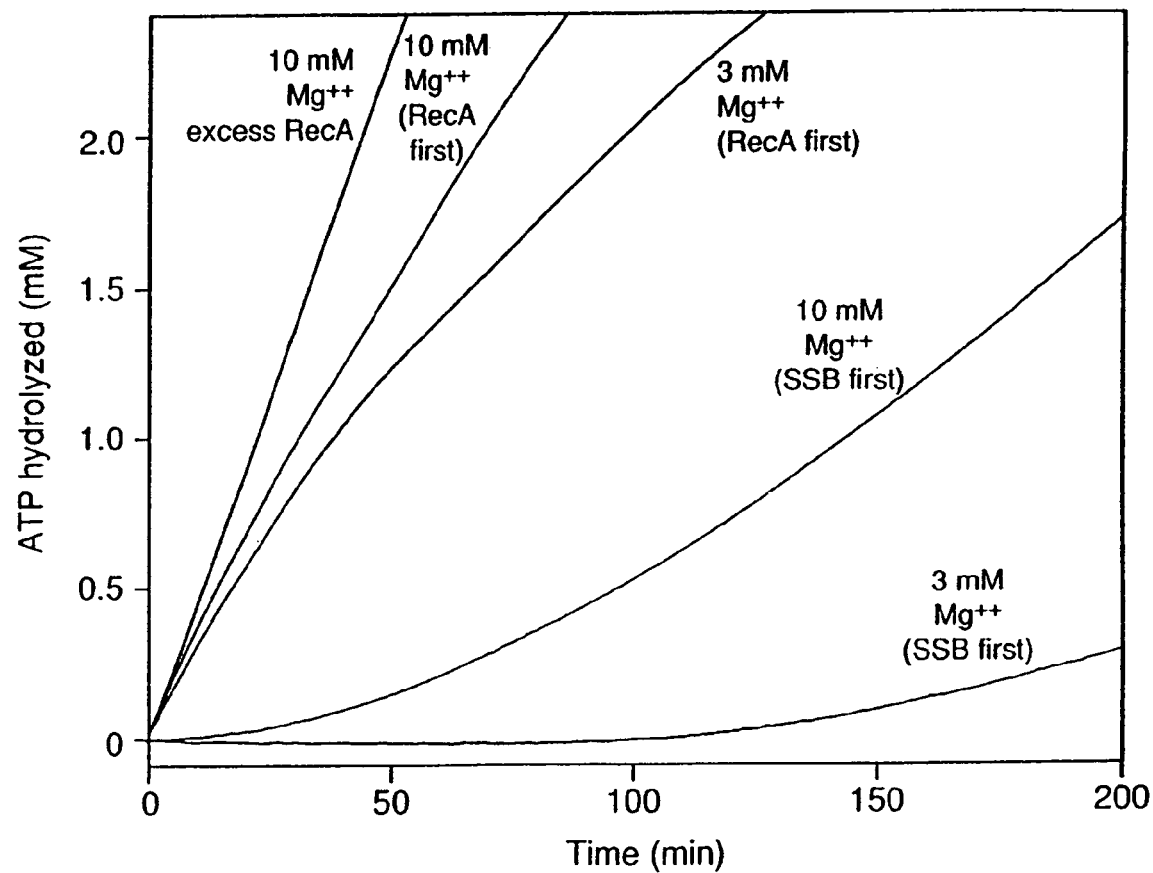
FIG. 1 shows the effects of SSB on wild-type RecA protein binding to circular ssDNA, with either RecA or SSB preincubated with the DNA at 3 and 10 mM $Mg^{2+}$.

The invention relates to novel RecA mutant proteins with certain mutations, which render the novel proteins highly proficient in SSB displacement and steady state binding of DNA as compared to the wild-type protein in the presence or absence of a DNA binding protein.

The invention encompasses a variety of embodiments. In one embodiment the invention provides a single mutant RecA protein having a deletion of at least 13–20 amino acid residues from the carboxyl terminus.

In a preferred embodiment the invention provides a single mutant RecA protein with 17 amino acid residues deleted from the carboxyl terminus, referred to herein as "RecAΔC17". The amino acid of sequence of RecAΔC17 is set forth herein as SEQ ID NO. 1 and its corresponding polynucleotide sequence is set forth herein as SEQ ID NO. 2.

This embodiment of the invention provides a single mutant RecA protein having an enhanced capacity to displace a DNA binding protein as compared to wild-type RecA. A preferable DNA binding protein is RPA and more preferable is SSB. Furthermore, this embodiment, suitably RecAΔC17, exhibits enhanced binding to DNA during a DNA strand exchange reaction as compared to wild-type RecA. RecA binding is measured through ATP hydrolysis assays described in the examples. A suitable DNA for the mutant protein, preferably RecAΔC17, to bind with is single-stranded DNA or a DNA with a secondary structure.

Furthermore, in a broader sense C-terminal deletions of RecA protein have been found to greatly enhance the capacity of the protein to compete with a DNA binding protein, suitably SSB. This enhanced DNA binding capacity was determined through conducting a series of C-terminal deletions systematically removing 6, 13 and 17 amino acids from the C-terminus of the wild-type RecA protein and characterizing them in detail (43 and 44, the contents of both is incorporated by reference here in its entirety). Through this series of deletions, it was found that removal of 13 amino acid residues was a suitable mutation, however, a preferred mutation was where 17 amino acids were deleted from the C-terminus of the wild-type RecA. In these studies it was also determined that a deletion of 25 amino acid residues was not preferred, in that this deletion mutant was unstable in many types of assays.

In yet another embodiment, it was found that the C-terminally truncated proteins of the invention, and especially the double mutant protein (RecAΔC17/E38K), dramatically alter the pH-reaction profile for DNA strand exchange. This unusual pH dependence for the mutant proteins of the invention has the potential to allow exquisite control over the entire reaction. Thus, it is envisioned that for the double mutant protein (RecAΔC17/E38K) at the lower pH values (pH 6–7), the first step of the DNA strand exchange (i.e., where a short segment of the duplex DNA is paired with the RecA-coated ssDNA to form hybrid intermediate DNA) proceeds very well. Large amounts of pairing intermediates appear in the reaction promoted by the C-terminally truncated mutant proteins. However, only at pHs above 7.5 can complete products be generated from the strand exchange reaction. Most suitably, the complete product formation in strand exchange reactions using the double mutant occurs at pH 8.5 (±1.0). Thus with the mutant proteins of the invention, a reaction can be initiated at low pH, held there in an intermediate stage without the reaction going to completion until desired. Then to push the strand exchange reaction towards completion, the pH is adjusted to the higher value.

Furthermore, the C-terminally truncated mutant proteins of the invention exhibit a progressive reduction in the requirement for free $Mg^{2+}$ in the same reaction (44). For the RecAΔC17 mutant protein, there is no measurable requirement for $Mg^{2+}$ in excess of that required to coordinate the ATP used in a given experiment (44). This is true also for the double mutant protein (RecAΔC17/E38K).

Another embodiment of the invention provides a double mutant RecA protein having a deletion of at least 13–25 amino acids residues from the carboxyl terminus and the amino acid change from a glutamate to a basic amino acid at position 38. A preferred embodiment of the invention provides a double mutant RecA protein having a 17 amino acid residue deleted from the carboxyl terminus and the amino acid change from a glutamate to arginine or even more preferably to lysine at position 38.

Applicants note that although the changes noted herein are disclosed in terms of changes at the protein level, it is well within the ability of a skilled artisan to modify a polynucleotide that encodes a RecA protein to encode the mutant proteins of the invention. The skilled artisan also understands the degeneracy of the genetic code and understands that a plurality of codons, made up of naturally occurring and synthetic nucleotides can direct the production of a single naturally occurring and synthetic amino acid residues. Thus, in practicing the invention, it is envisioned that modified amino acid residues having similarly basic properties may be substituted for glutamate at position 38.

The preferred embodiment of the invention has 17 amino acid residues deleted from the C-terminus and a lysine at position 38 and is referred to herein as "RecAΔC17/E38K". The amino acid of sequence of RecAΔC17/E38K is set forth herein as SEQ ID NO. 3 and its corresponding polynucleotide sequence is set forth herein as SEQ ID NO. 4.

In the RecA double mutant protein embodiment, suitably RecAΔC17/E38K, the mutant proteins have an enhanced capacity to displace a DNA binding protein as compared to wild-type RecA. A preferred DNA binding protein may be SSB or RPA. These mutant proteins have an increased steady-state DNA binding capacity during a DNA strand exchange reaction as compared to the wild-type RecA amino acid sequence, which is set forth herein as SEQ ID NO. 5. It is noted that the DNA to be bound by the mutant proteins of the invention may be single-stranded, double-stranded, linear or circular DNA. Furthermore, this embodiment allows for the induction of complete product formation in the DNA strand exchange reaction through an increase in the RecA reaction pH. To shift the RecA reaction towards complete product formation, a pH above 7.5 is preferable and a pH of 8.5 (±1.0) is most preferable. In addition to being pH-dependent, the double mutant proteins of the invention are also $Mg^{2+}$ concentration dependent. A preferred $Mg^{2+}$ concentration is 4–8 mM and most preferably 5 mM.

Figure 8:
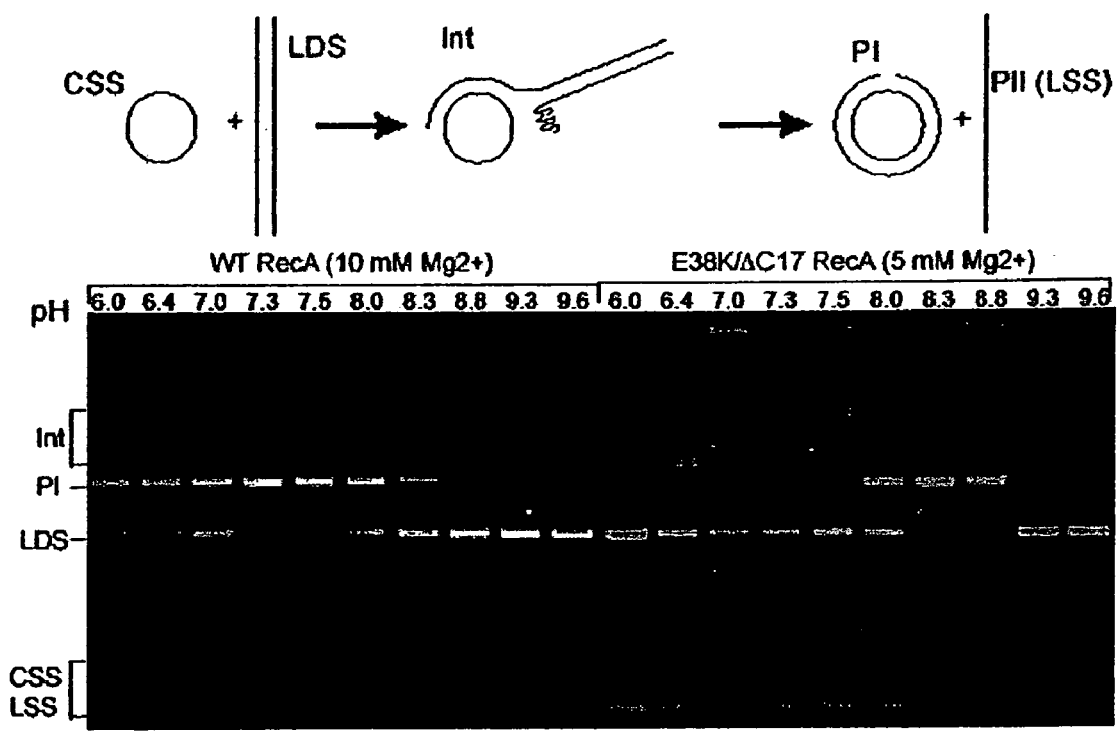
FIG. 8 shows a gel profiling the pH dependence of wild-type and E38K/ΔC17 mutant RecA in the DNA strand exchange reaction.

Furthermore, as described in the examples below, another embodiment of the invention provides a double mutant RecA protein, suitably RecAΔC17/E38K, which is capable of promoting a multiple-strand DNA exchange reaction. A suitable strand exchange reaction is between two homologous double-stranded DNAs (Four-stranded exchange reaction) and can overcome DNA structural barriers such as small heterologous insertions. These RecA activities require the hydrolysis of ATP and preferably may be carried out at the optimal pH and $Mg^{2+}$ concentration conditions. Similar to the four-strand exchange reaction, the three-strand exchange reaction is shown in FIG. 8, above the depiction of the gel. It is noted that the pH range for the four-stranded reaction is narrower than that of the three-stranded reaction.

In another embodiment the invention provides a method of catalyzing homologous DNA pairing and DNA strand exchange reactions in an in vitro or in vivo environment using a sufficient amount of either the single or double mutant RecA proteins of the invention. It is noted that the double mutant RecAΔC17/E38K displaces SSB somewhat better than any of the individual mutant proteins of the invention under some conditions, and exhibits a higher steady-state level of binding to linear ssDNA under all conditions.

Hence, methods of using the novel RecA mutant proteins and kits having the proteins as components thereof are also contemplated by the present invention, as described hereinbelow.

Finally, in accordance with the RecA mutant proteins of the invention, the effect of each mutation is described below in the examples and it is understood that the applicants have identified amino acid residues of the protein that have a direct impact upon function and that other modifications at the same positions can have effects comparable to, greater than or lesser than those noted.

Applicability of Novel Mutant RecA Proteins

Currently there are a number of companies selling the wild type RecA protein such as for example, Amersham Biosciences, Inc. (Piscataway, N.J.), New England Biolabs (Beverly, Mass.); Rockland Immunochemicals, Inc. (Gilbertsville, Pa.); Cambio Ltd. (Cambridge, England); Epicentre Technologies (Madison, Wis.); Roche Applied Sciences (Indianapolis, Ind.); Promega Corp. (Madison, Wis.); Active Motif, Inc. (Carlsbad, Calif.); United States Biological (Swampscott, Mass.); and USB Corp (Cleveland, Ohio). It is believed that the properties exhibited (i.e., enhanced ability to displace SSB, persistently bind DNA, pH-dependent regulation of strand displacement reaction, etc.) by the RecA mutant proteins of the invention, preferably RecAΔC17, and most preferably RecAΔC17/E38K enable these novel proteins to potentially replace wild-type and other existing RecA proteins for all current biotechnology applications using RecA and making new applications feasible. For example, it is envisioned that the tight-binding single and double mutants of the invention may be used to promote in vitro alterations of genes to permit the rapid construction of desired gene mutants for industrial and pharmaceutical purposes.

Furthermore, because the mutant proteins, preferably RecAΔC17, and most preferably RecAΔC17/E38K bind DNA more persistently to regions of secondary structure than the wild-type RecA protein, the RecA mutant proteins may be used to increase the efficiency of any application where the presence of the SSB protein may complicate concurrent or subsequent reactions.

Similarly, due to the tighter binding capacity of the mutant proteins of the invention, suitably RecA E38K/ΔC17, can provide a much more stable RecA platform for technologies that utilize RecA protein to select particular sequences or clones from complex mixtures using for an example the ClonCapture cDNA selection protocol (73–76). The RecA E38K/ΔC17 mutant protein of the invention would enhance cloning technologies like this by binding to DNA more persistently to make selection of suitable clones more efficient. In addition, by using a pH between 6 and 7, the motor function of the double mutant protein (which would tend to eliminate many clones after they were captured) may be attenuated. This should further enhance the efficiency with which RecA protein can be used in any technology designed to select a particular sequence from a complex mixture.

Another application where the RecA mutant proteins of the invention can be useful is in targeting the site-specific cleavage of small and large DNAs. In brief, RecA is bound to a short single stranded DNA that is complementary in sequence to the region to be cleaved. The RecA takes this DNA and pairs it with the DNA in a large chromosome or a complex mixture of DNA. The site thus bound is protected from additional enzymatic action. One can then methylate the sites of cleavage of a particular restriction enzyme, X. All the sites in the DNA that are recognized by that restriction system will be methylated, except for the one protected by the RecA complex. Then the RecA can be removed. The resulting DNA, when treated with restriction endonuclease X, will be cleaved only at the site that had been protected with RecA (methylation at the other sites prevents their cleavage) (64). Thus, RecA mutants may also be used to map genomes with the aid of limited restriction enzyme cleavage (64, 66–69).

Alternatively, the RecA mutant proteins of the invention, preferably RecAΔC17, and most preferably RecAΔC17/E38K may be used as the basis for the design and construction of tiny electronic circuits based on DNA. In brief, a complex DNA molecule is laid out on a support such as silicon. Oligonucleotides attached to gold particles or other metal clusters used to create a transistor, are targeted to specific spots along the DNA with the use of the RecA protein. Thus, the mutants of the invention would make the construction of such circuits more efficient, and make the constructed circuits more stable. In addition, the pH properties of the double mutant should also help make the paired RecA complexes bind more tightly (65).

Yet another application where the RecA mutant proteins of the invention can be useful is in facilitating the effort to develop methods for human gene therapy that must rely on the cellular recombination systems or alteration of genomes (70–72).

Therefore, it is envisioned that the RecA mutant proteins described by the invention, preferably RecAΔC17, and most preferably RecAΔC17/E38K can replace any commercially available wild-type RecA used in site-directed mutagenesis through displacement loop structures; targeted site-specific cleavage of small and large DNA; enrichment of target sequences from libraries or other DNA pools; visualization of DNA for electron microscopy (77); and cloning or other strategies involving use of RecA protein and a site-specific oligonucleotide to block endonuclease cleavage at the complementary site in a target DNA molecule.

The mutant proteins of the invention, preferably RecAΔC17, and most preferably RecAΔC17/E38K may be commercially distributed either as a single product to help promote homologous recombination through a multiple-step ATP-dependent pathway; promote proteolytic cleavage of repressors; or catalyzes DNA strand-pairing and exchange. The mutants of the invention may also be included as one of many components in a kit. For example a kit may include a single and/or a double RecA mutant of the invention from *E. coli* or any other suitable organism in a suitable storage buffer, and an instruction leaflet. A suitable storage buffer for the RecA mutants of the invention may include 50% glycerol containing 50 mM Tris-HCl (pH 7.5), 0.1 mM EDTA, and 1 mM DTT.

EXAMPLES

The following examples provide the materials and methods used to produce the various RecA mutants of the invention. Although applicants have exemplified a number of RecA mutant proteins differing from wild-type RecA at position 38 and at the C-terminus, one can reasonably predict from their analysis the effects of other related mutations based upon structure-function analysis.

Example 1

Proteins and Biochemicals

*E. coli* SSB was purified as described (47, the contents of which is incorporated by reference). SSB was stored in a buffer containing 20 mM Tris-HCl (pH 8.3), 1 mM EDTA, 50% glycerol, 1 mM β-mercaptoethanol and 500 mM NaCl. The concentration of the purified SSB protein was determined from the absorbance at 280 nm using the extinction coefficient of $2.83 \times 10^4$ $M^{-1}$ $cm^{-1}$ (48). *Saccharomyces cerevisiae* Replication Protein A (RPA) was purified as described (49, the contents of which is incorporated by reference here in its entirety). The concentration was determined by the absorbance at 280 nm using the extinction coefficient of $8.8 \times 10^4$ $M^{-1}$ $cm^{-1}$ (50). The wild-type RecA, RecAΔC6, RecAΔC13, and RecAΔC17 proteins were purified as described (43). RecA 441 was purified using the following modification to the wild-type RecA procedure previously described (43). The initial polyethylenimine pellet was washed with R buffer (20 mM Tris-HCl (80% cation, pH 7.5), 1 mM DTT, 0.1 mM EDTA, and 10% (w/v) glycerol) and 50 mM ammonium sulfate and extracted two times with R buffer+150 mM ammonium sulfate. The RecA E38K (RecA730) mutant protein was purified like the wild-type RecA protein, except that the final fraction was subjected to an additional step. The protein was loaded onto a PBE 94 column equilibrated with R buffer, and the column was developed with a linear gradient from 0 to 1.0 M KCl. The RecA E38K mutant was eluted at approximately 600 mM KCl. The eluted protein was dialyzed extensively against R buffer and concentrated as for the wild-type protein. The RecAΔC17/E38K double mutant protein was purified using the same protocol as the RecAΔC17 protein (43). The concentration of each RecA and RecA mutant protein was determined using the extinction coefficient of wild-type RecA, $2.23 \times 10^4$ $M^{-1}$ $cm^{-1}$ (51). Unless otherwise noted, all reagents were purchased from Fisher. Lactate dehydrogenase (LDH), pyruvate kinase (PK), phosphoenolpyruvate (PEP), nicotinamide adenine dinucleotide (reduced form) (NADH), and ATP were purchased from Sigma. PBE 94 resin was purchased from Amersham Pharmacia Biotech. DTT was purchased from Research Organics, Inc.

Example 2

DNA Substrates

All DNA concentrations are given in terms of total nucleotides. Poly(dT) was purchased from Amersham Pharmacia Biotech, and the approximate average length is 229 nt. The concentration of poly(dT) was determined by UV absorption at 260 nm using an extinction coefficient of 8.73 $mM^{-1}$ $cm^{-1}$. M13 mp8 bacteriophage circular ssDNA was prepared as described (52). The concentration of M13 mp8 ssDNA was determined by UV absorption at 260 nm using the extinction coefficient, 9.03 $mM^{-1}$ $cm^{-1}$.

Example 3

ATP Hydrolysis Assays

A coupled spectrophotometric enzyme assay (53 and 54, the contents of both is incorporated by reference here in their entirety) was used to measure the ssDNA-dependent ATPase activities of the wild-type RecA, RecAΔC6, RecAΔC13, and RecAΔC17 proteins. The regeneration of ATP from PEP and ADP was coupled to the oxidation of NADH and monitored by the decrease in absorbance of NADH at 380 nm. The 380 nm wavelength was used so that the signal remained within the linear range of the spectrophotometer for the duration of the experiment. The assays were carried out on a Varian Cary 300 dual beam spectrophotometer equipped with a temperature controller and a 12 position cell changer. The cell path length and band pass were 0.5 cm and 2 nm, respectively. The NADH extinction coefficient at 380 nm of 1.21 $mM^{-1}$ $cm^{-1}$ was used to calculate the rate of ATP hydrolysis.

The reactions were carried out at 37° C. in 25 mM Tris-OAc (80% cation), 1 mM DTT, 3 mM potassium glutamate, 5% (w/v) glycerol, an ATP regeneration system (10 U/mL PK, 1.92 mM PEP), and a coupling system (3 mM NADH and 10 U/mL LDH). The concentrations of DNA (M13 mp8 ssDNA or poly(dT)), RecA protein (wild-type RecA, RecAΔC6, RecAΔC13, RecAΔC17, RecA 441, RecA E38K or RecAΔC17/E38K), Mg(OAc)$_2$, and SSB or RPA are indicated in the description of each experiment hereinbelow. To initiate the assay, the ssDNA was preincubated with either a RecA protein, or a ssDNA binding protein (SSB or RPA), for 10 minutes at 37° C. Then SSB or a RecA protein, respectively, was added. ATP was added to 3 mM final concentration, either with the RecA protein, or SSB or RPA, as indicated. Data collection was then begun. In reactions in which no ssDNA binding protein is included, SSB storage buffer is added instead. In the salt titrations, conditions were the same as above on poly(dT), except without SSB or SSB storage buffer. After a steady-state rate was achieved, aliquots of concentrated NaCl were added, allowing the reactions to come to steady state between additions.

After the various single and double mutants of the invention were produced their abilities to compete with SSB for binding to single stranded and double stranded DNA were compared with the wild-type RecA protein. To measure RecA binding to DNA, rate of ATP hydrolysis was measured using a coupled enzyme assay described hereinabove (53, 54). RecA protein hydrolyzes ATP when bound to DNA, and the ATPase rate is proportional to the amount of RecA bound under most conditions (7,53,55). This assay was also shown to represent a reliable and real-time method to monitor SSB displacement by RecA when SSB is prebound to ssDNA (8).

Example 4

SSB Competition with Wild-Type RecA Protein for Binding to M13 mp8 ssDNA

The outcome of the competition between SSB and RecA for binding to circular bacteriophage M13 mp8 ssDNA strongly depends on the relative concentrations of the proteins, which protein is preincubated with the ssDNA, and on the $Mg^{2+}$ concentration (7,9). As FIG. 1 illustrates, when the RecA protein is present at concentrations stoichiometric with its available DNA binding sites (3 nt ssDNA per RecA monomer), RecA displaces prebound SSB from M13 mp8 ssDNA quite slowly at 3 mM $Mg^{2+}$.

In referring to FIG. 1, DNA binding was monitored indirectly by following the DNA-dependent ATPase activity of RecA protein. Reactions were carried out as described in Experimental Procedures, and contained 5 μM M13 mp8 ssDNA, 1.67 μM or 2.5 μM RecA protein, 0.5 μM SSB protein, 3 mM ATP, and 3 or 10 mM $Mg(OAc)_2$, as indicated in the figure. Either RecA or SSB was preincubated with the ssDNA for 10 minutes before the final protein addition (RecA first or SSB first reactions, respectively). RecA was added to 2.5 μM only in the reaction indicated in the figure as containing excess RecA, with RecA prebound at 10 mM $Mg^{2+}$, otherwise the RecA was present at 1.67 μM. In each experiment, ATP was added with the SSB.

This $Mg^{2+}$ concentration is stoichiometric to the ATP concentration used in the experiment. At 10 mM $Mg^{2+}$, the SSB is displaced much more quickly upon RecA addition. If, however, RecA is preincubated with the M13 mp8 ssDNA at 3 nt/monomer, some RecA protein is gradually displaced in the presence of SSB, but the initial rates of ATP hydrolysis indicate a high level of RecA binding. The rates decline somewhat with time, but remain much higher than the initial rates observed when SSB was preincubated with the ssDNA. RecA protein again competes with SSB somewhat better at 10 mM $Mg^{2+}$ than at 3 mM $Mg^{2+}$. The decline in rates indicate that the DNA is not completely bound by RecA when RecA is present at these stoichiometric levels, affording SSB significant access to the DNA. When the RecA concentration is increased 50% (2 nt/monomer), so the excess RecA ensures coverage of the DNA, RecA is not displaced by SSB when the RecA is bound to the DNA prior to the SSB (FIG. 1).

Example 5

SSB Competes with Wild-Type RecA Protein for Binding to Poly(dT) ssDNA

Figure 2:
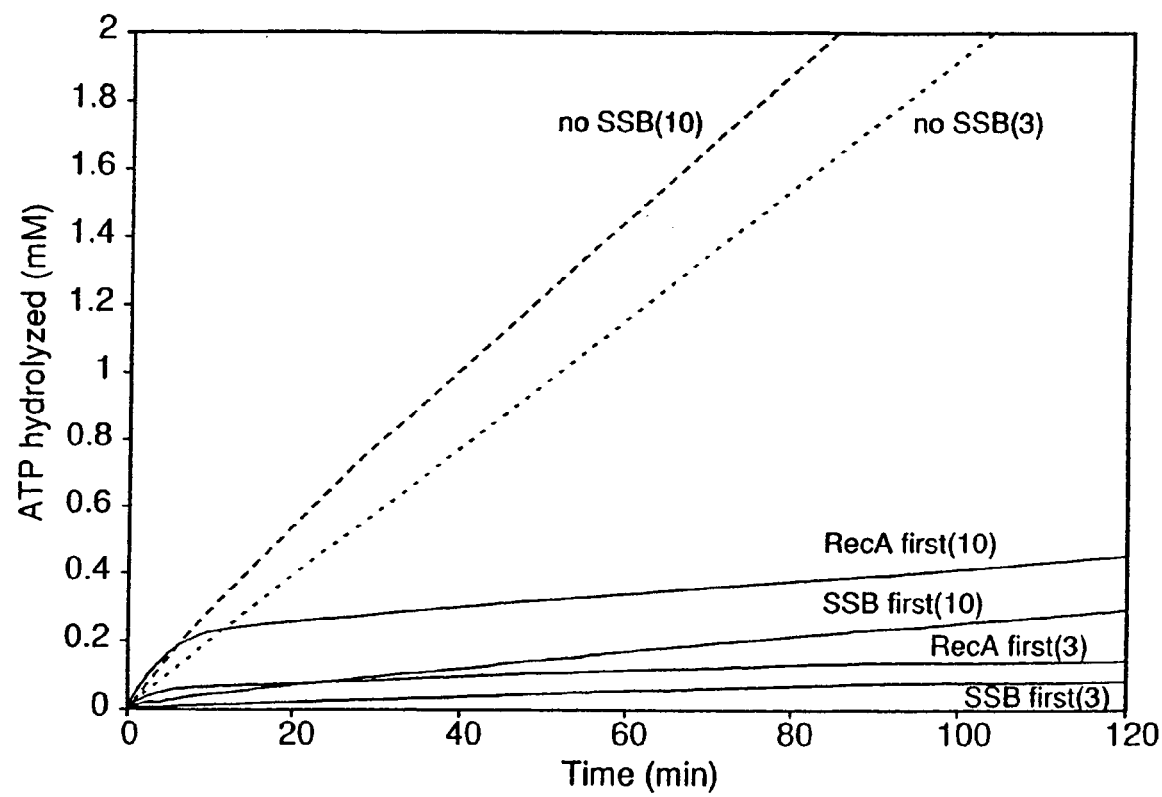
FIG. 2 shows the effects of SSB on wild-type RecA protein binding to poly(dT) ssDNA, with either RecA or SSB preincubated with the DNA at 3 and 10 mM $Mg^{2+}$.

A complication in the study of SSB effects on wild-type RecA binding to M13 mp8 ssDNA at various $Mg^{2+}$ concentrations is that SSB can remove $Mg^{2+}$-induced secondary structure in M13 mp8 ssDNA, which otherwise inhibits RecA binding (7,57). Thus SSB has a stimulatory effect on RecA filament formation as well as a competitive, inhibitory effect. In order to eliminate this stimulatory contribution from SSB, poly(dT) ssDNA was used in place of M13 mp8 ssDNA. Previously it was shown that much more prebound RecA is displaced from poly(dT) by SSB than from M13 mp8 ssDNA (7). This occurs to a large extent because of end-dependent disassembly of RecA filaments (5,56,58), which is readily observed only on linear DNAs where filament extension at one end does not compensate for disassembly at the other. Here it is shown that at 10 mM $Mg^{2+}$, wild-type RecA protein (3 nt/monomer) is almost completely displaced from poly(dT) by SSB in a process that is complete in less than 10 minutes (FIG. 2). In referring to FIG. 2, DNA binding was monitored as described in the legend to FIG. 1. Reactions contained 5 μM poly(dT) ssDNA, 1.67 μM RecA protein, 0.7 μM SSB, 3 mM ATP, and 3 or 10 mM $Mg(OAc)_2$, as indicated in parentheses in the figure. Either RecA or SSB was preincubated with the ssDNA for 10 minutes before the final protein addition. For the controls, denoted by dashed lines, SSB was replaced with SSB storage buffer. In each experiment, ATP was added with the SSB or SSB storage buffer.

At 3 mM $Mg^{2+}$, the displacement of RecA by SSB is considerably faster. RecA added to poly(dT) prebound with SSB is not able to appreciably displace the SSB at 3 or 10 mM $Mg^{2+}$, indicating that binding of SSB to poly(dT) is highly favored over RecA binding to the linear poly(dT). Unlike the case with M13 mp8 ssDNA, the resulting steady-state rates are the same regardless if RecA or SSB is preincubated with the ssDNA. In these experiments, the ATP is added with the SSB, and thus ATP is not included in the RecA preincubation in the experiments where RecA is added first. However, including ATP in the RecA preincubation had no discernable effect on the results shown (data not shown). As previously observed, a small net disassembly occurs in the absence of SSB, as indicated by the slight decline in the rate of ATP hydrolysis with time (dashed lines in FIG. 2), and disassembly and reassembly of filaments is doubtlessly occurring at a steady state (5,56,58). The rate of hydrolysis by RecA protein in the absence of SSB is somewhat higher at 10 mM $Mg^{2+}$ than at 3 mM.

Example 6

The Capacity of RecA Protein to Compete with SSB is Enhanced With Progressive Deletion of the C-Terminal Amino Acids The C-terminus of RecA contains a number of acidic residues. As shown in FIG. 3A, deletions of 6, 13 or 17 amino acids from the C-terminus progressively remove a total of three, six or seven glutamate and aspartate residues. In referring to FIG. 3A, DNA binding was monitored indirectly by following the DNA-dependent ATPase activity of RecA protein. Panel A highlights the C-terminal region of RecA protein. The core domain, which includes the P-loop (ATP binding motif), is shown in white. The shaded and black regions of the sequence correspond to the N-terminal and C-terminal domains, respectively. The primary structure of the C-terminal 17 amino acids of the RecA protein is diagramed below the linear sequence. The hexagons highlight the high concentration of negatively charged amino acids in this region. The arrows indicate points of truncation in the deletion mutants: RecAΔC6, RecAΔC13 and RecAΔC17.

The ability of these mutant proteins to compete with SSB was tested and compared with that of wild-type RecA protein. At 3 mM $Mg^{2+}$, where wild-type RecA has the least capacity to compete with SSB for binding to poly(dT), RecAΔC13, and to an even greater extent, RecAΔC17, bind well to the poly(dT) that has been prebound with SSB (FIG. 3B). At 3 mM $Mg^{2+}$, RecAΔC6 is unable to compete with SSB. Thus, in preparing the mutants of the present invention, suitable RecA mutants will have a carboxyl terminus deletion of between 13 and 25 amino acids. It is believed that having a carboxyl terminus deletion of between 13–20 amino acids is preferable and having 17 amino acids is most preferable.

The ATPase reactions of each protein in the absence of SSB are also displayed in FIG. 3B to show that at 3 mM $Mg^{2+}$, in the absence of SSB, each protein binds to poly(dT) to approximately the same extent. The apparent $k_{cat}$ for ATP hydrolysis by wild-type RecA (calculated by assuming that all of the DNA is bound by RecA protein) in these reactions is 11.5 $min^{-1}$, quite comparable to rates with poly(dT) observed previously (7). However, as shown below, this rate is lower than the nearly 30 min$^{-1}$ rate observed when RecA is carefully titrated onto circular ssDNA. The lower rate almost certainly reflects incomplete binding of the DNA, and perhaps an equilibrium state in which filaments are undergoing steady-state end-dependent assembly and disassembly.

Example 7

SSB Displacement by the Mutant RecA Proteins is Enhanced by Mg2+

All of the RecA proteins including RecAΔC6, compete more effectively with SSB at 10 mM Mg$^{2+}$, and at 10 mM Mg$^{2+}$ it is more evident that RecA's ability to compete with SSB increases with progressive deletion of RecA's C-terminus (FIG. 3C). The RecAΔC17 mutant protein exhibits no detectable lag in binding, indicating a particularly rapid SSB displacement process. Each RecA protein binds poly(dT) efficiently in the absence of SSB at 10 mM Mg$^{2+}$.

When M13 mp8 ssDNA is used, the outcome of the wild-type RecA-SSB competition is highly dependent on which protein is preincubated with the ssDNA (FIG. 1) (7,9). However, when poly(dT) is used the resulting steady-state rates are the same no matter which protein is preincubated with the ssDNA (FIG. 2). It was found that for RecAΔC17 protein, the steady-state rates are also the same whether RecAΔC17 or SSB is preincubated with poly(dT) (FIG. 3C and data not shown). When RecAΔC17 was preincubated with poly(dT) and ATP, and then challenged with SSB, the challenge had no measurable effect on the rate of ATP hydrolysis at 10 mM Mg$^{2+}$, and by inference on the state of RecAΔC17 binding. At 3 mM Mg$^{2+}$, there is a slow decline in ATPase rate occurring over approximately 60 minutes after the challenge, after which the rate seen in FIG. 3C is observed (data not shown). This suggests a slow displacement of the mutant RecA protein by the SSB.

Thus, in referring to the data shown in FIGS. 3B and 3C, reactions contained 0.7 µM SSB, 1.67 µM RecA protein, 5 µM poly(dT) ssDNA, 3 mM ATP and either 3 mM (B) or 10 mM (C) Mg(OAc)$_2$. In all reactions, ATP and SSB were preincubated with the ssDNA for 10 minutes before the addition of the RecA protein indicated in the figure. The controls without SSB for each RecA mutant protein are shown as dashed lines, and substituted SSB storage buffer for the SSB. At the point where these dashed lines are bisected by the vertical labeling line, the listing of the proteins (top to bottom) corresponds to the top to bottom positioning of the dashed lines (the top line is the reaction of the wild-type RecA protein, etc). Wild-type RecA protein is denoted WT in this and subsequent figures.

Example 8

Figure 3:
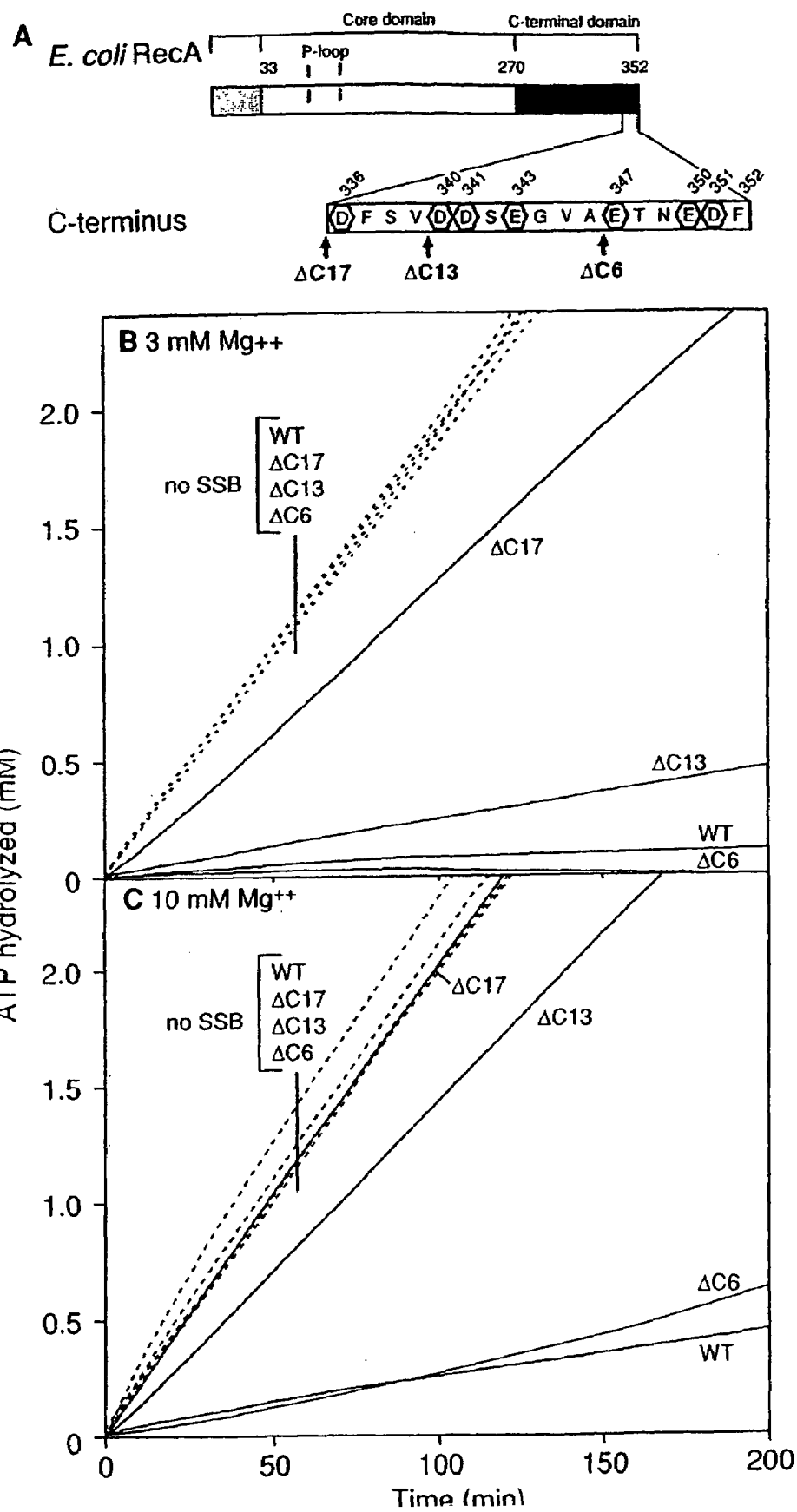
FIGS. 3A–C shows the displacement of SSB from poly (dT) by wild-type RecA protein and C-terminally truncated RecA proteins ΔC6, ΔC13 and ΔC17, at 3 and 10 mM $Mg^{2+}$.
Figure 4:
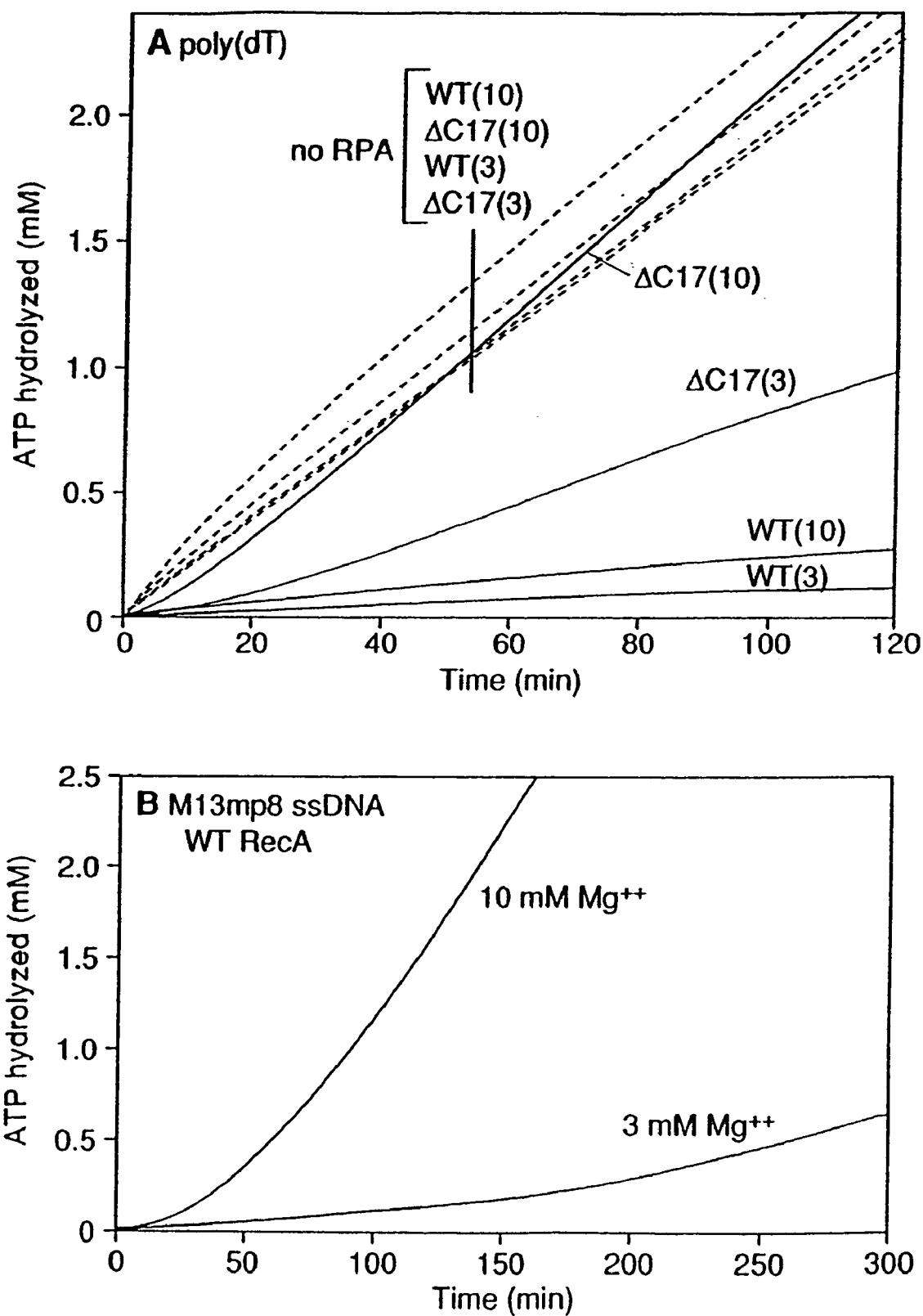
FIGS. 4A and B shows the displacement of RPA from poly(dT) by wild-type RecA protein and C-terminally truncated RecA proteins AC6, ΔC13 and ΔC17.

The Capacity of RecA Protein to Compete With RPA is Progressively Enhanced as Deletion of the C-Terminus of RecA is Increased Both the wild-type and C-terminally truncated RecA proteins are better able to compete with SSB at 10 mM Mg$^{2+}$ than at 3 mM Mg$^{2+}$ (FIGS. 1, 3B and 3C). This difference could be due to effects of Mg$^{2+}$ either on the RecA proteins or on SSB. Mg$^{2+}$ is known to affect the cooperativity of the different binding modes of SSB (59). An increase in Mg$^{2+}$ could lower the cooperativity of binding of SSB, which in turn could affect its ability to compete with RecA protein. Therefore, it was investigated whether Mg$^{2+}$ stimulated the competition of RecA with RPA, a ssDNA binding protein whose binding, unpublished studies indicate, is not affected by Mg$^{2+}$. Additionally, it was asked whether the inhibition of wild-type RecA protein was due to a specific protein—protein interaction with SSB mediated through the C-terminal region of RecA. Removal of this region would then result in the ability of C-terminally truncated RecA protein to compete with SSB, as shown in FIGS. 3B and 3C. However, as illustrated in FIG. 4A, the same result obtained with SSB is seen with RPA. At 3 and 10 mM Mg$^{2+}$, wild-type RecA has a limited capacity to compete with RPA for binding to poly(dT). In contrast, RecAΔC17 does bind to poly(dT) coated with RPA and is especially proficient at 10 mM Mg$^{2+}$ (FIG. 4A). In referring to FIG. 4A, DNA binding by RecA and RecA mutants was monitored indirectly by following the DNA-dependent ATPase activity of RecA protein. Reactions in panel A contained 0.6 µM RPA, 1.67 µM RecA protein, 5 µM poly(dT) ssDNA, 3 mM ATP and either 3 mM or 10 mM Mg(OAc)$_2$ as indicated by the number in parentheses. RPA was preincubated with the ssDNA for 10 minutes before the addition of the RecA protein indicated in the figure. Controls carried out in the absence of RPA (dashed lines) are labeled as indicated in the legend to FIG. 3. This suggests that Mg$^{2+}$ has a significant enhancing effect on RecA protein function in SSB displacement even when the C-terminus is removed.

Additional experiments were carried out with the wild-type RecA protein and M13 mp8 circular ssDNA, to examine the effects of Mg$^{2+}$ under conditions in which filament disassembly at filament ends would minimally affect the results. SSB was preincubated with the ssDNA. With this circular DNA substrate, the RecA protein can slowly displace the SSB at 3 mM Mg$^{2+}$ (FIG. 4B). FIG. 4B refers to two reactions with wild-type RecA carried out under the same conditions as panel A, but with M13 mp8 ssDNA replacing the poly(dT) which shows that the displacement is considerably faster at 10 mM Mg$^{2+}$.

Displacement of SSB by RecA C-terminal truncation mutants is apparently not due to a higher inherent affinity for ssDNA. The ability of RecA protein to bind DNA in the presence of increasing NaCl concentration correlates with its inherent DNA affinity (49). Binding to poly(dT) was monitored indirectly with the DNA-dependent ATPase assay in the absence of SSB, and as a function of increasing NaCl concentration (data not shown). The half-maximal binding point (taken as the NaCl concentration where the ATPase activity is halved relative to the maximum) is seen at approximately 750 mM NaCl for the wild-type protein, decreasing slightly to about 700 mM under these conditions for the RecAΔC17 mutant.

Example 9

Figure 5:
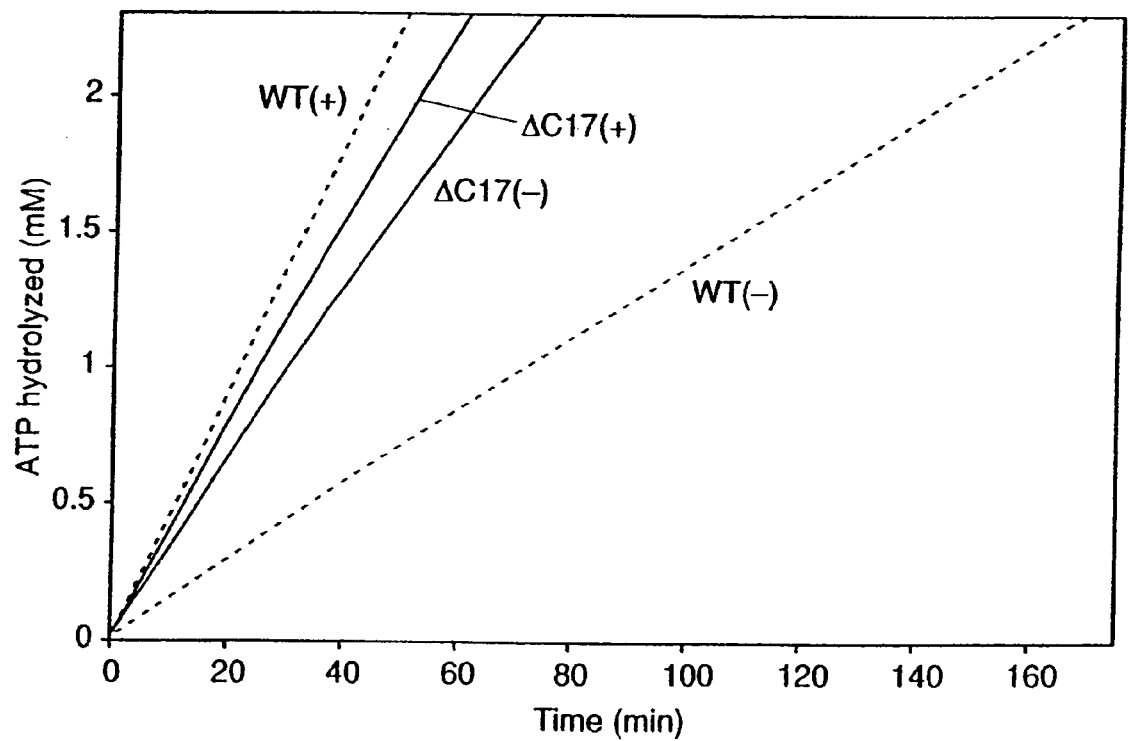
FIG. 5 shows a comparison of the capacity of wild-type RecA protein to bind to secondary structure-containing M13 mp8 ssDNA with that of the RecAΔC17 protein.

RecAΔC17 Protein Binds M13 mp8 ssDNA with Secondary Structure Better Than Does Wild-Type RecA Protein RecA E38K and RecA803, which have been demonstrated to compete with SSB for binding to ssDNA more effectively than wild-type RecA, appear to also bind to regions of secondary structure in ssDNA better than the wild-type protein (8). It was investigated whether RecAΔC17 was more capable than wild-type RecA at binding M13 mp8 ssDNA that contains secondary structure, induced by 10 mM Mg$^{2+}$, in the absence of SSB. In these experiments the RecA was present at 2 nt/monomer to prevent RecA displacement in the control experiments that contained SSB. As illustrated in FIG. 5, the rate of ATP hydrolysis of wild-type RecA protein prebound to M13 mp8 ssDNA in the presence of SSB and 10 mM Mg$^{2+}$ drops significantly when SSB is omitted, to 30% of the rate in the presence of SSB (dashed lines in FIG. 5).

In referring to FIG. 5, the DNA binding by wild-type and C-terminally truncated RecA protein was monitored indirectly by following the DNA-dependent ATPase activity of RecA protein. Reactions were carried out as described in Experimental Procedures, and contained 5 μM M13 mp8 ssDNA, 2.5 μM RecA protein, 3 μM ATP, and 10 mM Mg(OAc)$_2$. Some reactions also contained 0.5 μM SSB as indicated (+in parentheses). Wild-type RecA protein or RecAΔC17 were preincubated the ssDNA for 10 minutes, before the addition of ATP and either SSB (+) or SSB storage buffer (−). The reactions with wild-type RecA protein are shown with dashed lines to highlight the contrast with the reactions with the RecAΔC17 mutant, which exhibit a much reduced effect of SSB addition.

This is consistent with a considerably reduced binding to the ssDNA under these conditions, as observed previously for RecA binding to ssDNA with appreciable secondary structure in the absence of SSB (7). In contrast, the ATPase rate of RecAΔC17 at 10 mM Mg$^{2+}$ drops only a little upon omission of SSB, to 84% of the rate seen with SSB (FIG. 5). In sum, the data indicate that RecAΔC17 is better able to bind DNA that contains secondary structure than is wild-type RecA.

Example 10

Improved SSB Displacement and Increased Steady-State DNA Binding With RecAΔC17/E38K The C-terminal region of the wild-type RecA protein negatively modulates the capacity of RecA to compete with the SSB protein for ssDNA binding sites. When the C-terminal residues are removed progressively (6, 13 and 17 residues) the mutant proteins exhibit a progressive increase in the capacity of RecA to displace SSB. The E38K point mutation also enhances this capacity. To demonstrate that a mutant protein with both the RecAΔC17 and the E38K mutations is much more effective at binding ssDNA and displacing SSB from ssDNA in vitro a comparison was made of RecA (wild-type), RecAΔC13, RecAΔC17, RecA441 double mutant (E38K+I298V), RecA E38K and RecAΔC17/E38K (17 residue C-terminal truncation combined with the RecA E38K mutation), as shown in FIG. 6.

Figure 6:
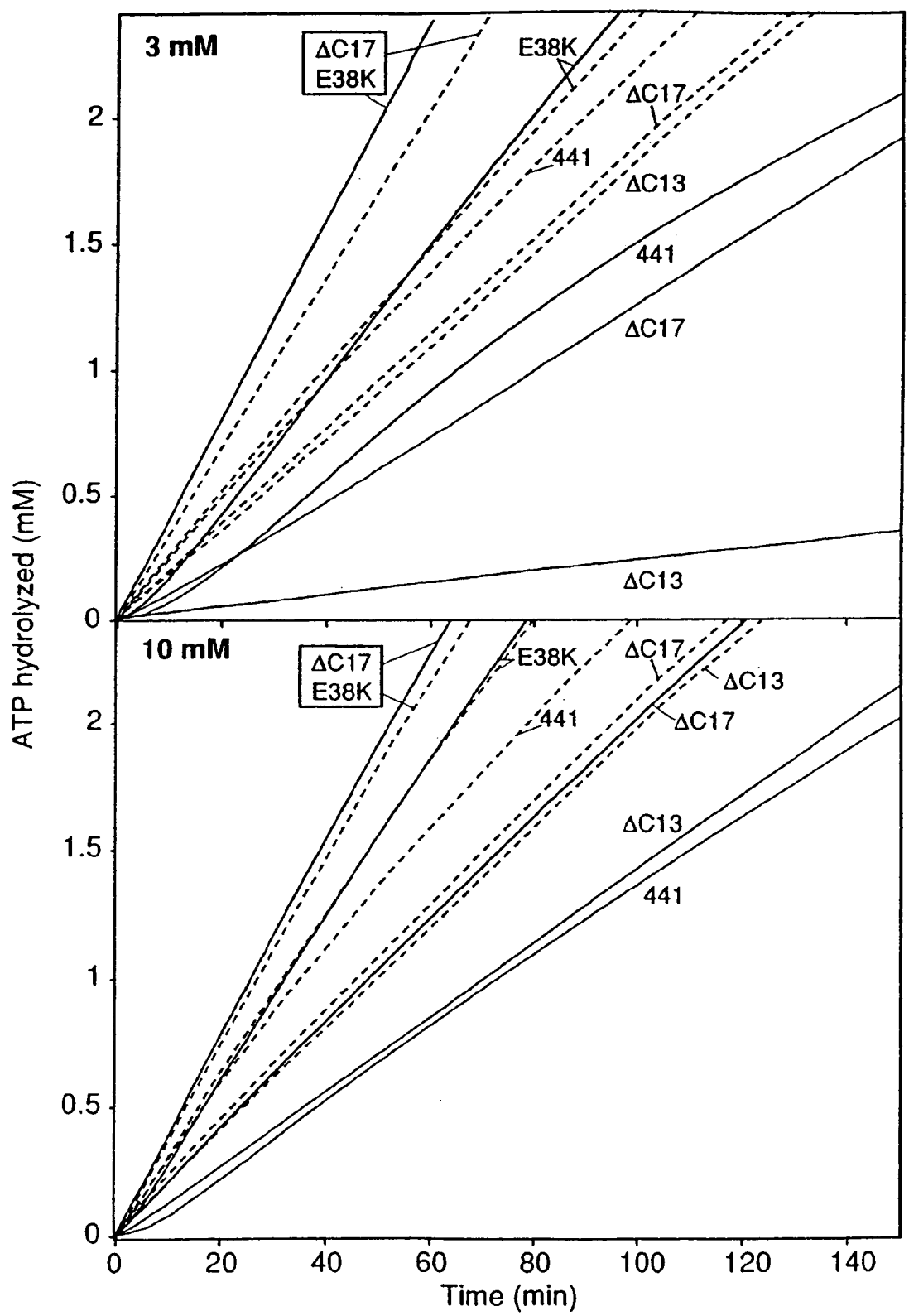
FIG. 6 shows a comparison of the SSB displacement and ssDNA binding activities of various RecA mutants proteins added to SSB-prebound poly(dT) ssDNA: RecA (wild-type), RecAΔC13, RecAΔC17, RecA 441, RecA E38K and RecA RecAΔC17/E38K.

In referring to FIG. 6, the DNA binding by RecA and RecA mutant proteins was monitored indirectly by following the DNA-dependent ATPase activity of RecA protein. Reactions contained 0.7 μM SSB, 1.67 μM RecA or RecA mutant protein, 5 μM poly(dT) ssDNA, 3 μM ATP and either 3 mM (FIG. 6A) or 10 mM (FIG. 6B) Mg(OAc)$_2$. In all reactions, SSB and ATP were preincubated with the ssDNA for 10 minutes before the addition of the RecA protein indicated in the figure. The controls without SSB for each RecA mutants are shown as dashed lines.

At 3 mM Mg$^{2+}$, the RecA441 mutant was similar to the RecAΔC17 mutant in its capacity to displace SSB. The RecA E38K mutant was the best of the individual mutants in this activity. A short but discernable lag in reaching a steady state of ATP hydrolysis was observed for each of the individual mutants. At 10 mM Mg$^{2+}$, the activity of the RecA441 mutant was similar to that of RecAΔC13, and less than that of RecAΔC17. The RecA E38K mutant was still the best individual mutant in SSB displacement. The lag in reaching an apparent steady state was reduced for all of the individual mutant proteins. When the RecAΔC17 and E38K mutations were combined in a single protein, a further enhancement was observed in SSB displacement and ssDNA binding. Furthermore, there was no discernable lag in ATP hydrolysis with the double mutant protein under any condition tested, and a substantially higher steady-state rate of ATP hydrolysis (with an apparent $k_{cat}$ in excess of 20 min$^{-1}$). It is noted that the ATP hydrolysis was higher in the presence of SSB than in its absence, a property observed with no other RecA mutant. It is envisioned that the higher rates of ATP hydrolysis could reflect a higher intrinsic rate of ATP hydrolysis by the double mutant protein. Alternatively, they could reflect a greater steady-state level of binding to the DNA.

Figure 7:
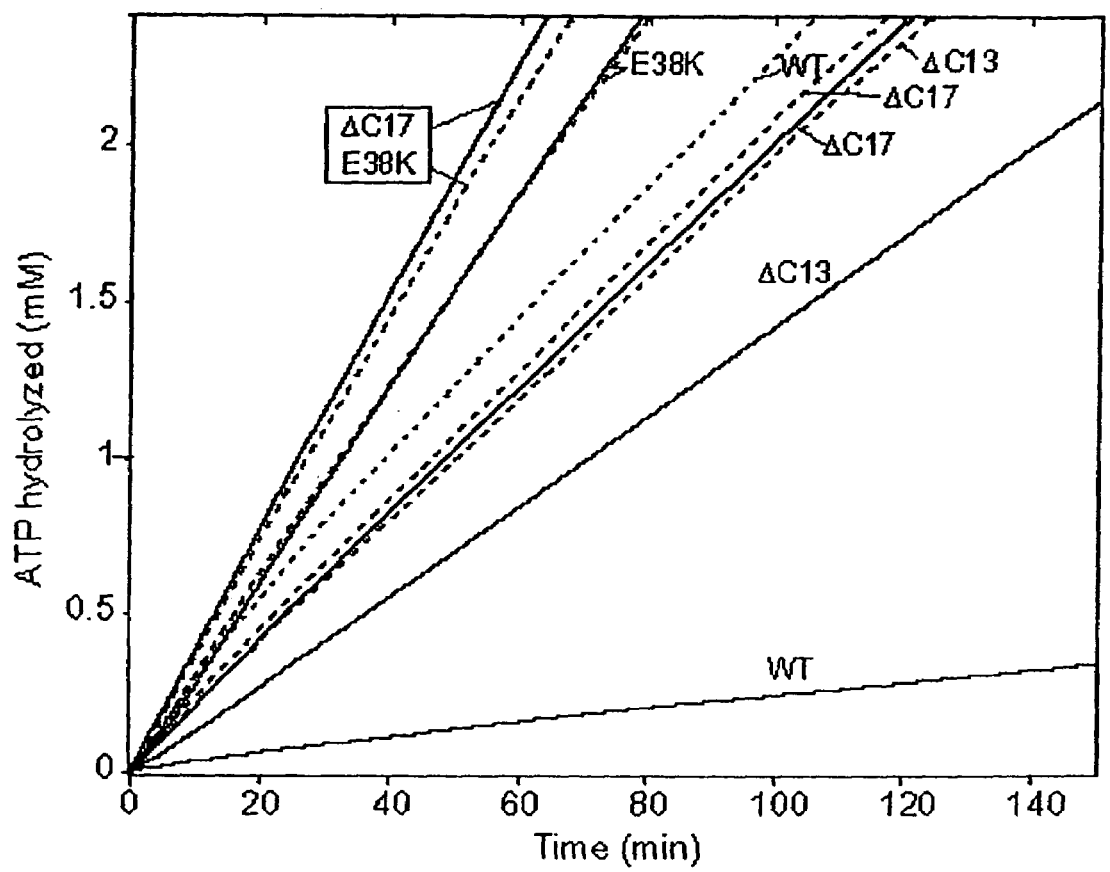
FIG. 7 shows a comparison of the SSB displacement and ssDNA binding activities of various RecA mutant proteins added to SSB-prebound poly(dT) ssDNA: RecA (wild-type; WT), RecAΔC17, ΔC13, E38K and E38K/ΔC17.

At the low Mg$^{2+}$ concentration, the double mutant protein was more effective at SSB displacement than either single mutant (FIGS. 6 and 7). In referring to FIG. 7, the DNA binding by RecA and RecA mutant proteins was monitored indirectly by measuring the DNA-dependent ATPase activity of the RecA protein. Reactions contained 0.7 μM SSB, 1.67 μM RecA, 5 μM poly(dT) ssDNA, 3 mM ATP and 10 mM magnesium ion. In all reactions, SSB and ATP were preincubated with the ssDNA for 10 min before the addition of the indicated RecA protein. The dashed lines indicate control experiments in which the SSB protein was omitted. Again, the experimental data indicates that the E38K/ΔC17 protein displaces the SSB protein better than either individual mutant protein. The presence of SSB does not inhibit the binding of E38K/ΔC17 protein to ssDNA. The enhancement of SSB displacement appears not to simply be due to a higher inherent affinity for ssDNA.

It is also encompassed within the invention that the C-terminal deletion mutants described herein may be combined with other RecA mutations, such as other point mutations to produce a variety of desired characteristics for RecA, such as improved displacement of DNA binding proteins and enhanced steady-state DNA binding.

Example 11

Double Stranded DNA Binding with RecAΔC17/E38K

In accordance with the invention, the RecA protein hydrolyzes ATP in a DNA-dependent manner. The apparent ATP hydrolysis rate correlates well with the binding of RecA on DNA because the activity at steady state is almost constant between pH 6 to pH 9. The wild-type RecA protein exhibits a long lag in binding to dsDNA, reflecting a slow nucleation step, at close to and above physiological pH. At this pH, wild-type RecA exhibits net disassembly from linear dsDNA. The lag for dsDNA binding is shortened as E38K/ΔC17<ΔC17<E38K<<wild-type at pH 7.3. The RecA E38K/ΔC17 protein exhibits almost no lag in binding to dsDNA and exhibits no measurable net disassembly from either linear or circular dsDNA at pH 7.3. Thus, the RecA E38K/ΔC17 double mutant of the invention binds to DNA more persistently than any RecA mutant described to date.

Example 12 pH Reaction Profile for DNA Strand Exchange with RecA E38K/ΔC17

The RecA double mutant E38K/ΔC17 protein of the invention exhibits a pH reaction-profile in which the steps of DNA strand exchange can be separated in a pH-dependent manner. The DNA strand exchange has two major steps. First, a short segment of the duplex DNA is paired with the RecA-coated ssDNA. This process requires ATP but not its hydrolysis. Second, the hybrid DNA created in the first step is extended in a phase that depends on ATP hydrolysis. In the wild type protein, both phases of the reaction occur over a broad pH range.

Figure 9:
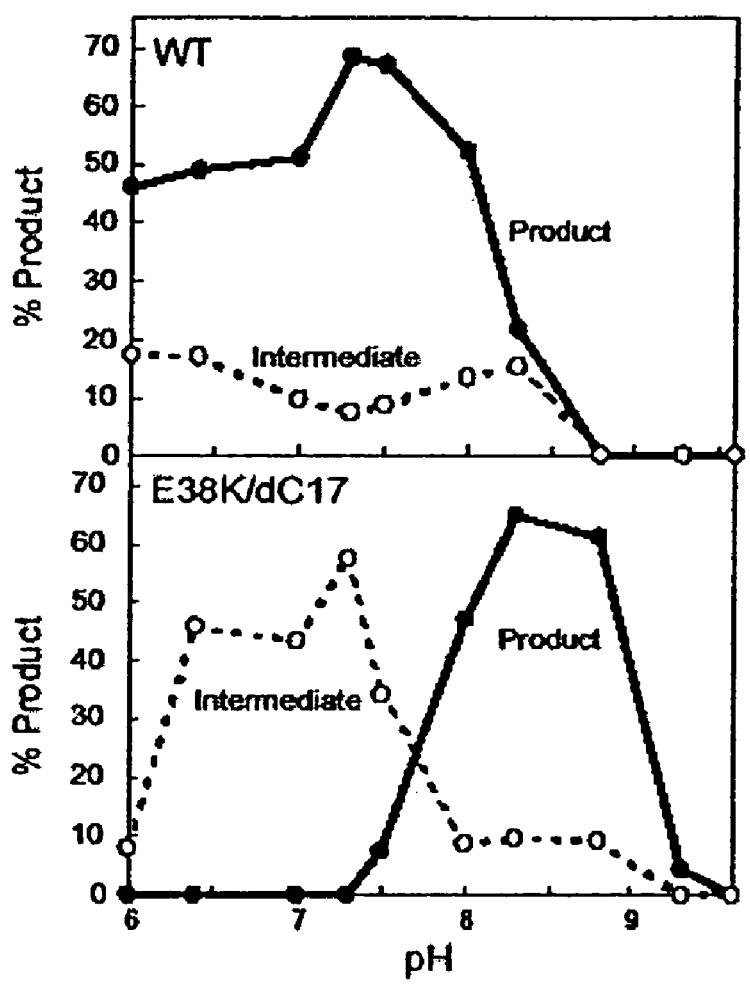
FIG. 9 shows a pH-reaction profile for DNA strand exchange reaction. The intermediates (open circle) and products (closed circle) promoted by wild-type and E38K/ ΔC17 RecA proteins were quantitated from FIG. 7 as a function of pH.
Figure 10:
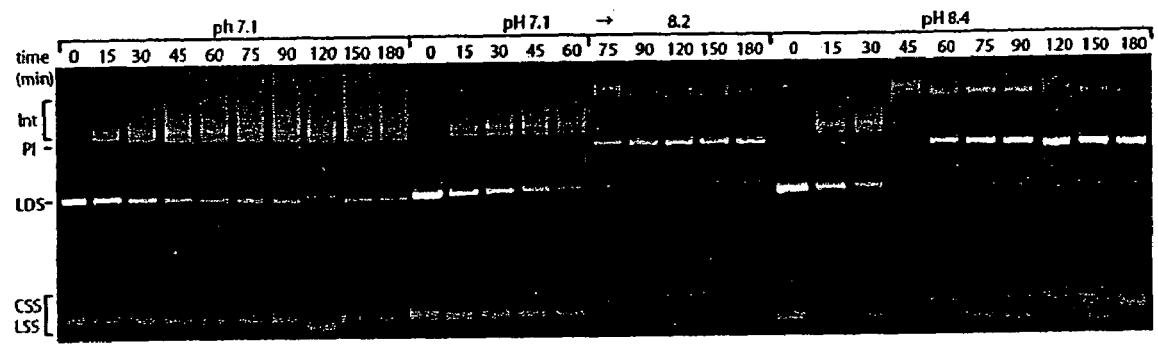
FIG. 10 shows a gel profiling the rate of strand exchange as a function of pH.

The formation of intermediates can be seen only at lower pHs and the formation of complete products in the second phase of the RecA reaction is seen only at pHs above 7.5 shown in FIGS. 8, 9 and 10. The optimum pH for complete product formation is shifted to pH 8.5 (±1.0). In referring to FIG. 8, the reactions were carried out in 25 mM buffer (varied as indicated to alter pH), 3 mM potassium glutamate, 1 mM DTT, 5% (w/v) glycerol, 2.2 mM phosphoenolpyruvate and 10 units/ml pyruvate kinase. 10 mM and 5 mM Mg(OAc)$_2$ were used for wild-type and E38K/ΔC17 RecA, respectively. RecA proteins (3.5 μM) were pre-incubated with 10 μM M13 mp7 circular ssDNA for 10 min. ATP (3 mM) and SSB (2 μM) were then added, followed by another 20 min incubation. The reaction was initiated by the addition of M13 mp7 linear double stranded DNA (to 10 μM), and further incubated for 2 hours at 37° C. The reaction was stopped by deproteinization with 10 mM EDTA, 1% SDS and 1 mg/ml Proteinase K and loaded on 1% agarose gel. Similarly, FIG. 9 refers to the pH-reaction profile for DNA strand exchange reaction, where the intermediates (open circle) and products (closed circle) promoted by wild-type and RecA E38K/ΔC17 proteins were quantitated from FIG. 7 as a function of pH.

Also, FIG. 10 further provides evidence that RecA E38K/ΔC17 protein is pH-dependent in catalyzing the formation of complete products in the strand exchange reaction. In referring to FIG. 10, the reactions were carried out as described in FIG. 8, except reaction aliquots were taken out at specified each time point. The reaction at pH 7.1 (left panel) exhibited the intermediate but no product, and reaction at pH 8.4 (right panel) exhibited the product after 60 min. In the middle panel, the pH of reaction was shifted from 7.1 to 8.2 at 60 min, and product appeared 15 min after pH was shifted (75 min).

Therefore, the formation of complete products in the second phase is seen only at pHs above 7.5, and the optimum is shifted to pH 8.5 (±1.0) in the double mutant is a notable difference between the E38K/ΔC17 and the wild-type RecA proteins. These results suggest that the range of pH conditions under which the E38K/ΔC17 protein can promote the complete (final) products of DNA strand exchange is quite narrow compared to the wild-type and individual mutant RecA proteins. This unusual pH dependence for the mutant proteins of the invention has the potential to allow exquisite control over the entire reaction.

In practicing the present invention, it is envisioned that at the lower pH values (pH 6–7), for the first step of the DNA strand exchange (i.e., where short segment of the duplex DNA is paired with the RecA-coated ssDNA to form hybrid intermediate DNA) proceeds very well. Large amounts of pairing intermediates appear in the reaction promoted by the mutant proteins, suitably the RecA E38K/ΔC17 protein. However, even after three hours the intermediates are not converted to products. Only at pHs above 7.5 can complete products be generated. Most suitably, the complete product formation in strand exchange reactions using the double mutant occurs at pH 8.5 (±1.0). With the wild-type protein, these intermediates appear at the early stage of the reaction and are smoothly converted to products over the entire active pH range. Thus with the mutant proteins of the invention, a reaction can be initiated at low pH, held there in an intermediate stage without the reaction going to completion until desired. Then to push the strand exchange reaction towards completion, the pH is adjusted to the higher value.

Example 13

Mg$^{2+}$ Ion Effect on the RecA E38K/ΔC17 Protein

The DNA strand exchange reaction mediated by the wild-type RecA protein requires 6–8 mM free Mg$^{2+}$ in the excess of that required for coordination of ATP. The requirement for free Mg$^{2+}$ is also exhibited by the E38K individual mutant. The removal of the C-terminal 17 amino acid residues eliminates the requirement for excess Mg$^{2+}$ (44). Therefore, the optimal concentration of Mg$^{2+}$ for the DNA strand exchange reaction catalyzed by the ΔC 17 individual mutant is equivalent to (as opposed to in excess of) the ATP concentration. This characteristic of the RecAΔC17 mutant indicates that the C terminus is involved in a Mg$^{2+}$-dependent conformational change required to activate the RecA protein for homologous pairing. The requirement for Mg$^{2+}$ in the E38K/ΔC17 protein mediate strand exchange closely parallels that of the ΔC17 individual mutant. However, the pH-reaction profile of the RecA protein is dependent on the Mg$^{2+}$ concentration, even for the reactions promoted by the E38K/ΔC17 and ΔC17 proteins. Roughly, the pH-profile is broadened with increasing Mg$^{2+}$ concentration (although the reaction diminishes overall as the Mg$^{2+}$ concentration is increased). As described hereinabove, the RecA E38K/ΔC17 double mutant protein-mediated reaction has a very narrow pH-reaction profile when the Mg$^{2+}$ concentration is equivalent to the ATP concentration. In practicing the invention a Mg$^{2+}$ concentration of 5 mM (with 3 mM ATP) is most suitable to mediate the strand exchange reaction using the double mutant.

Example 14

Extended Reactions with RecA E38K/ΔC17

The wild-type RecA protein can also promote a strand exchange reaction between two homologous double-stranded DNA (Four-stranded exchange reaction) and can overcome DNA structural barriers such as small heterologous insertions. These RecA activities require the hydrolysis of ATP. Likewise, in practicing the invention the RecA E38K/ΔC17 mutant can also promote these two reactions provided that the reaction is carried out at the optimal pH and Mg$^{2+}$ concentration conditions. The optimal pH for the four-strand exchange reaction is similar to, albeit slightly narrower than, the range of pH for promoting the three-strand exchange reaction shown in FIG. 8, above the depiction of the gel. Below pH 7, large amounts of intermediate molecules accumulate in the four-strand exchange reaction promoted by RecA E38K/ΔC17. These intermediates are not converted to products, as in the reactions shown in FIGS. 8 and 9. Thus, in multiple strand exchange reactions, the RecA E38K/ΔC17 double mutant can facilitate complete products formation only when the pH is shifted to a range between 7.5–9.5 and more suitably between 8–9.

DISCUSSION

From these results it was concluded that the C-terminal region of wild-type RecA protein negatively modulates the capacity of wild-type RecA to compete with SSB for binding to ssDNA. Progressive removal of 6, 13 and 17 amino acids from the C-terminus of RecA results in a progressive increase in the capacity of RecA to displace SSB. RecAΔC17 also displaces RPA from ssDNA much more readily than wild-type RecA. The binding of RecAΔC17 to DNA containing secondary structure is enhanced relative to wild-type RecA. The capacity of these C-terminally truncated mutants to compete with SSB is quite high, especially in the case of RecAΔC17. The RecAΔC17 truncation and the E38K mutation work together in a double mutant to eliminate a discernable lag in SSB displacement under some conditions and to increase the steady-state level of DNA binding by RecA.

The inhibition of RecA protein binding to ssDNA by SSB could be mediated by specific protein—protein interactions, or it could reflect a simple competition for DNA binding sites. For example, SSB could inhibit the binding of wild-type RecA protein by means of specific protein—protein interactions with the RecA C-terminus, which would be progressively eliminated in the C-terminally truncated RecA proteins. Such a mechanism would imply species specificity. This possibility was examined by substituting RPA, the ssDNA binding protein from S. cerevisiae, for SSB. It was found that RPA competes efficiently with wild-type RecA for binding to ssDNA, and that the C-terminally truncated RecA proteins exhibit a progressively enhanced capacity to displace RPA. This indicates that the function of the RecA C-terminus does not involve a species-specific interaction.

Furthermore, it has been found that excess $Mg^{2+}$ (above that required to coordinate with ATP) has a stimulatory effect on the displacement of SSB by RecA protein, over and above the enhancement conferred by the C-terminal deletions, as previously observed for wild-type RecA (7). For all of the RecA mutants and for wild-type RecA, SSB displacement is more facile in the presence of 10 mM $Mg^{2+}$ than it is at 3 mM $Mg^{2+}$. This could reflect an alteration of the binding state of SSB, or an effect on RecA protein itself. SSB has multiple salt-dependent DNA binding modes (30, 59) that might differentially affect SSB's ability to compete with RecA protein for ssDNA binding sites. The experiments that substituted RPA for SSB had a second purpose, to attempt to address the source of the stimulation by $Mg^{2+}$. Unpublished experiments suggest that RPA does not have multiple salt-dependent DNA binding modes of the sort observed with SSB, and that $Mg^{2+}$ does not stimulate the binding of ssDNA by RPA.

It was found that the ability of the C-terminally truncated RecA proteins and wild-type RecA to compete with RPA is stimulated by the higher $Mg^{2+}$ concentration, suggesting that the excess $Mg^{2+}$ is directly affecting the RecA protein. It is envisioned by the invention that the $Mg^{2+}$ may be acting on SSB, as well, to alter its function in this system. It has been hypothesized that a $Mg^{2+}$ interaction site might exist in the E. coli RecA C-terminus, where it could be mediated by the many glutamate and aspartate residues present there (44). To the extent that $Mg^{2+}$ does not affect RPA binding, the $Mg^{2+}$ effects in experiments with SSB appear to be due largely to effects of $Mg^{2+}$ on the RecA protein. Since this is true for even the RecAΔC17 mutant, there may be a $Mg^{2+}$ interaction site or sites on RecA protein outside of the C-terminus that affect the capacity of RecA to displace SSB. In contrast, an interaction of $Mg^{2+}$ with these sites does not appear to be required for the strand exchange reaction, as the excess $Mg^{2+}$ requirement in that reaction was largely eliminated for RecAΔC17 (44).

Also, it has been found that the addition of the volume-occupying agents polyethylene glycol and polyvinyl alcohol to RecA-mediated strand exchange reactions both greatly reduced the excess $Mg^{2+}$ requirement in strand exchange and increased the ability of RecA to compete with SSB for ssDNA (60). This result, combined with similar results using RecAΔC17 protein, suggests that volume-occupying agents may stabilize a conformation of the C-terminus of RecA that does not inhibit these activities. This conformation may be the same one induced by addition of excess $Mg^{2+}$. Removal of the C-terminus also alleviates the inhibition. The present invention also envisions that the addition of $Mg^{2+}$, addition of volume-occupying agents or removal of the C-terminus may expose the RecA DNA binding site in such a way that RecA is better able to compete with SSB and RPA, or is better able to extract ssDNA from the surface of these binding proteins.

It is useful to compare the properties of the C-terminally truncated mutant RecA proteins with those of other RecA mutant proteins shown to have an increased ability to compete with SSB for ssDNA. A primary question is the mechanism by which RecA mutants might have an enhanced ability to compete with SSB. Using a salt titration midpoint assay, which reflects RecA's equilibrium DNA affinity (61), it was found that the inherent DNA affinity of RecAΔC17 for poly(dT) is not appreciably changed from that of wild-type RecA (data not shown). Previous studies of RecA mutant proteins that compete better with SSB than wild-type RecA have shown that the properties of these proteins, RecA803 (V37M), RecA441 (E38K+I298V), and RecA E38K, are also not due to an increased ssDNA binding affinity (8,28, 62). The capacity of these previously characterized RecA mutant proteins to compete with SSB was shown to correlate with their rate of association with DNA, a characteristic also found with wild-type RecA protein in the presence of volume-occupying agents (60).

In accordance with this invention, it has been shown that the SSB displacement and steady-state DNA binding of the 17 residue C-terminal deletion mutant protein are improved further by the E38K mutation. The double mutant displaces SSB with no lag that is measurable in these experiments, and provides a higher steady-state level of DNA binding on linear poly(dT) in the presence of SSB than any mutant studied to date. Since the intrinsic ATPase activity of the double mutant is the same as that of the individual mutant proteins, the increase in steady-state ATP hydrolysis is attributed to an increase in the steady-state level of DNA binding. These results suggest that SSB displacement and/or overall DNA binding is modulated by several different parts of the RecA protein. It has been proposed that the negative charges of the C-terminus were part of a regulatory network of protein surface salt bridges (44).

It is believed that the increase in SSB displacement and overall DNA binding observed when the deletion of the C-terminal 17 residues and the replacement of an acidic residue with a basic residue at position 38 are combined could also reflect particular disruptions of an extensive salt bridge network. Hence, the double mutant appears to bind to DNA better in the presence of SSB than in its absence. To date no explanation for this effect is known.

However, upon further characterization, it is noted that the RecA E38K/ΔC17 double mutant exhibits almost no lag in binding to dsDNA and exhibits no measurable net disassembly from either linear or circular dsDNA at pH 7.3 compared to the wild-type RecA protein which exhibits a long lag in binding to dsDNA, reflecting a slow nucleation step, at close to and above physiological pH. Furthermore, the RecA double mutant E38K/ΔC17 protein of the invention exhibits a pH reaction-profile in which the steps of DNA strand exchange can be separated in a pH-dependent manner, where the formation of complete products is seen only at pHs above 7.5, and the optimum is shifted to pH 8.5 (±1.0). This unusual pH dependence has the potential to allow exquisite control over the entire reaction, particularly when the $Mg^{2+}$ concentration is similar to the ATP concentration. Thus with the double mutant, a reaction can be initiated at low pH, held there, and the reaction not be completed until the pH is adjusted to the higher value.

It is further noted that RecAC17 shares an additional property with RecA E38K and RecA803, an increased proficiency compared to wild-type RecA of competing with secondary structure for ssDNA binding sites (8,28). While the rates of ATP hydrolysis for RecA E38K and RecA803 on M13 mp8 ssDNA at 10 mM $Mg^{2+}$ in the presence of SSB were similar to that of wild-type protein, the rates of the mutant proteins in the absence of SSB were much higher than that of wild-type RecA. In addition, the RecA E38K, RecA803 and wild-type proteins all bound equally well to etheno M13 mp8 DNA, which does not contain secondary structure. A similar result was obtained for RecAΔC17. The ATPase rate for wild-type RecA on M13 mp8 ssDNA at 10 mM $Mg^{2+}$ in the absence of SSB is 30% of the rate in the presence of SSB. In contrast, the ATPase rate of RecAΔC17 at 10 mM $Mg^{2+}$ drops only a moderate amount upon omission of SSB, to 84%. In sum, the data indicates that RecAΔC17, like RecA803 and RecA E38K, is better able to bind DNA that contains secondary structure than is wild-type RecA.

In accordance with the invention, it is envisioned that the regulation of RecA's DNA binding ability and/or its ability to compete with SSB would allow RecA to gain access to SSB-coated DNA only at the appropriate time, such as after a replication fork stalls. The binding of RecA to ssDNA that has been previously bound with SSB is facilitated by the RecO and RecR mediator proteins (5,63). The examples described by the invention suggest that these mediator proteins alter the binding of SSB to ssDNA, creating a nucleation site for RecA filament formation. The work presented here indicates that RecA possesses an inherent and robust capacity to displace SSB, but that this capacity is suppressed by the C-terminus. This suggests another potential mechanism of mediator protein action. The RecO and RecR proteins might interact directly with RecA protein during the filament nucleation process, altering RecA conformation so that the C-terminus is no longer inhibitory.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A isolated double mutant *Escherichia Coli* RecA protein comprising a truncation of from 13 to 25 amino acid residues; from the carboxyl terminus and an amino acid change from a glutamate to a basic amino acid at position 38.

2. The protein of claim 1 wherein the truncation is 17 amino acid residues from the carboxyl terminus.

3. The protein of claim 1 wherein the basic amino acid is lysine.

4. The protein of claim 1 wherein the basic amino acid is to arginine.

5. The protein of claim 1 wherein 17 amino acid residues are truncated from the carboxyl terminus and the glutamate is changed to lysine, as set forth in SEQ ID NO. 3.

6. The protein of claim 5 comprising an enhanced capacity to displace a DNA binding protein as compared to wild-type RecA.

7. The protein of claim 6 wherein the protein is a single stranded DNA binding protein, SSB.

8. The protein of claim 5 comprising an increased steady-state DNA binding capacity during a DNA strand exchange reaction as compared to wild-type RecA.

9. The protein of claim 8 wherein the DNA is single-stranded.

10. The protein of claim 8 wherein the DNA is double-stranded.

11. The protein of claim 10 wherein the double-stranded DNA is linear or circular.

12. The protein of claim 8 wherein the DNA strand exchange reaction is pH dependent.

13. The protein of claim 12 wherein the DNA strand exchange reaction induces complete product formation between a pH of 8.0 to 9.0.

14. The protein of claim 12 wherein the DNA strand exchange reaction induces complete product formation at a pH of 8.5.

15. The protein of claim 8 wherein the DNA strand exchange reaction is Mg2+ concentration dependent.

16. The protein of claim 15 wherein the Mg2+ concentration is between 4 mM–8 mM.

17. The protein of claim 15 wherein the Mg2+ concentration is 5 mM.

18. The protein of claim 5 wherein the protein promotes an extended reaction, wherein the extended reaction is at least a three-strand exchange reaction.

19. A kit comprising the protein of claim 1.

20. A kit comprising the protein of claim 5.

21. An isolated double mutant *E. Coli* RecA protein comprising; a truncation of up to 17 amino acid residues from the carboxyl terminus and an amino acid change from a glutamate to a basic amino acid at position 38.

22. A kit comprising the protein of claim 21.

23. An isolated double mutant *E. Coli* RecA protein comprising a truncation of from 13 to 20 amino acid residues; from the carboxyl terminus and an amino acid change from a glutamate to a basic amino acid at position 38.

24. An isolated double mutant *E. Coli* RecA protein comprising a truncation of from 13 to 17 amino acid residues; from the carboxyl terminus and an amino acid change from a glutamate to a basic amino acid at position 38.

* * * * *